United States Patent
Yi et al.

(10) Patent No.: US 10,568,579 B2
(45) Date of Patent: Feb. 25, 2020

(54) PRESSURE SENSOR INCLUDING HYBRID ELECTRONIC SHEET AND WEARABLE DEVICE INCLUDING THE PRESSURE SENSOR

(71) Applicant: KOREA INSTITUTE OF SCIENCE AND TECHNOLOGY, Seoul (KR)

(72) Inventors: Hyun Jung Yi, Seoul (KR); Seung Woo Lee, Seoul (KR); Ki Young Lee, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 569 days.

(21) Appl. No.: 14/988,459

(22) Filed: Jan. 5, 2016

(65) Prior Publication Data

US 2016/0287089 A1     Oct. 6, 2016

(30) Foreign Application Priority Data

Apr. 2, 2015   (KR) .......................... 10-2015-0046751

(51) Int. Cl.
| | |
|---|---|
| A61B 5/00 | (2006.01) |
| A61B 5/0215 | (2006.01) |
| A61B 5/021 | (2006.01) |
| A61B 5/103 | (2006.01) |

(52) U.S. Cl.
CPC .......... *A61B 5/6897* (2013.01); *A61B 5/0215* (2013.01); *A61B 5/02108* (2013.01); *A61B 5/1036* (2013.01); *A61B 2562/028* (2013.01); *A61B 2562/0247* (2013.01)

(58) Field of Classification Search
None
See application file for complete search history.

(56) References Cited

U.S. PATENT DOCUMENTS

| | | | |
|---|---|---|---|
| 7,574,792 B2 * | 8/2009 | O'Brien | A61B 5/0031 29/600 |
| 8,161,826 B1 * | 4/2012 | Taylor | G01L 1/18 73/862.044 |
| 8,627,716 B2 | 1/2014 | Son | |
| 9,493,764 B2 | 11/2016 | Yi et al. | |
| 10,017,537 B2 | 7/2018 | Yi et al. | |

(Continued)

FOREIGN PATENT DOCUMENTS

| | | |
|---|---|---|
| CN | 101111750 A | 1/2008 |
| CN | 201622147 U | 11/2010 |

(Continued)

OTHER PUBLICATIONS

Cui et al., Chemical Functionalization of Graphene Enabled by Phage Displayed Peptides, 2010, NANO letters, vol. 10, pp. 4559-4565, published on Oct. 13, 2010 (Year: 2010).*

(Continued)

*Primary Examiner* — Michael R Bloch
(74) *Attorney, Agent, or Firm* — Goldilocks Zone IP Law

(57) ABSTRACT

Provided are a pressure sensor including hybrid electronic sheet and a wearable device including the pressure sensor. The pressure sensor has excellent controllable electric characteristics and excellent mechanical flexibility and stability, and measures, for example, pressure in a simple and highly reproducible manner in which a resistance of a component in a sensor varies depending on applied pressure.

18 Claims, 20 Drawing Sheets

Specification includes a Sequence Listing.

(56) References Cited

U.S. PATENT DOCUMENTS

| | | | |
|---|---|---|---|
| 2005/0147964 A1 | 7/2005 | Yamakawa et al. | |
| 2006/0287602 A1* | 12/2006 | O'Brien | A61B 5/0031 |
| | | | 600/486 |
| 2007/0117147 A1 | 5/2007 | Jagota et al. | |
| 2007/0264623 A1 | 11/2007 | Wang et al. | |
| 2007/0281321 A1 | 12/2007 | Nagale et al. | |
| 2008/0087543 A1 | 4/2008 | Bae et al. | |
| 2011/0053737 A1* | 3/2011 | Chang | A63B 69/34 |
| | | | 482/83 |
| 2012/0245444 A1 | 9/2012 | Otis et al. | |
| 2013/0053666 A1 | 2/2013 | Hughes et al. | |
| 2014/0174927 A1 | 6/2014 | Bashir et al. | |
| 2014/0249052 A1 | 9/2014 | Mehmet et al. | |
| 2017/0204400 A1 | 7/2017 | van der Donk et al. | |

FOREIGN PATENT DOCUMENTS

| | | | | |
|---|---|---|---|---|
| CN | 102308270 A | 1/2012 | | |
| CN | 103946364 A | 7/2014 | | |
| JP | H01-253627 A | 10/1989 | | |
| KR | 1020100079579 A | 7/2010 | | |
| KR | 102012053797 A | 5/2012 | | |
| WO | 96/26674 A1 | 9/1996 | | |
| WO | 99/20649 A1 | 4/1999 | | |
| WO | WO-9920649 A1 * | 4/1999 | | B82Y 5/00 |
| WO | 2006060226 A1 | 6/2006 | | |
| WO | 2013052318 A1 | 4/2013 | | |

OTHER PUBLICATIONS

Communications of Chinese Patent Application No. 201610065711. 6, which corresponds to this application.

Razmi et al.,Graphene quantumdotsasanewsubstrateforimmobilizat ionanddirect electrochemistryofglucoseoxidase: Applicationtosensitive glucose determination, Biosensors and Bioelectronics, Sep. 28, 2012, pp. 498-504, Elsevier.

Jia et al. Electrochemical Tattoo Biosensors for Real-Time Noninvasive Lactate Monitoring in Human Perspiration, Analytical Chemistry, Jul. 1, 2013 , pp. 6553-6560, vol. 85, ACS Publications, USA.

Yao et al., A contact lens with embedded sensor for monitoring tear, glucose level, NIH Public Access Author Manuscript, Mar. 15, 2011, pp. 3290-3296, vol. 7, Biosens Bioelectron, USA.

Zhang et al. A novel glucose biosensor based on direct electrochemistry of glucose oxidase incorporated in biomediated gold nanoparticles-carbon nanotubes composite film, Sensors and Actuators B158 , Apr. 27, 2011, pp. 23-27. Elsevier.

Search Report from the WIPO dated Jan. 14, 2016, in a counterpart PCT/KR2015/010060, which is a counterpart PCT application of co-pending U.S. Appl. No. 14/740,691.

Sachdev S. Sidhu , Engineering M13 for phage display, Biomolecular Engineering , Jun. 12, 2001, pp. 57-63, Nov. 18.

* cited by examiner

Conductive nanomesh
transferred on patterned PDMS

PRESSURE SENSOR INCLUDING HYBRID ELECTRONIC SHEET AND WEARABLE DEVICE INCLUDING THE PRESSURE SENSOR

CROSS-REFERENCE TO RELATED APPLICATION

This application claims the benefit of Korean Patent Application No. 10-2015-0046751, filed on Apr. 2, 2015, in the Korean Intellectual Property Office, the disclosure of which is incorporated herein in its entirety by reference.

BACKGROUND

1. Field

One or more exemplary embodiments relate to a pressure sensor including a hybrid electronic sheet and a wearable device including the pressure sensor.

2. Description of the Related Art

Pressure sensors are widely used due to the commercial availability and popularity of mobile terminals or displays to which a touch-input manner is introduced. Touch-based pressure sensors are attracting attention for use in robots that measure and respond to external environments or stimuli, as well as use in electronic devices. Due to increasing recognition for the ubiquitous environment and technical development of humanoid robots, in addition to process robots that receive one-dimensional commands and repeatedly perform correspondingly, robots that respond and handle complicated and various environments or external stimuli by themselves are getting much attention. To voluntarily respond to external stimuli or environmental changes, such robots convert external stimuli or environmental changes into electrical signals through a tactile pressure sensing system mounted on their surfaces and voluntarily, flexibly respond to a command of a user.

Flexible device-based pressure sensors are available for use in, in addition to emotional electronic devices and humanoid robots, a sensor system that manages physical activities and regular sports activities. Flexible device-based super-sensitive pressure sensors can be used in a wearable sensor system that measures a heart pulse wave via the human skin or collects data about human walking and habits by attaching a pressure sensor to the sole of footwear. To embody such a wearable sensor system, there is a need to develop a sensor that includes a sensor basic unit having excellent bending and restoring properties, and excellent mechanical flexibility and stability.

Silicon-based solid MEMS-based pressure devices have a high level of accuracy, but due to their fragile property, they lack flexibility and are likely to crack, resulting in high difficulty for their application on various surfaces including a flexible surface. To develop a novel flexible electronic device having high mechanical flexibility, a conductive polymer, such as polypyrrole, PEDOT:PSS, or polyaniline, graphene, or a nano-structure material, such as carbon nanotube (CNT), metal nanoparticle, or metal nanowire are getting attention as an alternative to silicon. In particular, CNT is an alternative to ITO, which is conventionally used, due to its high light transmissibility and conductivity. CNT also has excellent chemical stability and mechanical characteristics. Furthermore, the recent advance in synthesis technology enables mass-production of CNT, decreasing manufacturing costs thereof. However, in the case of conductive polymer-based pressure sensors, their long-term stability and, when in contact with moisture, their conductivity may change significantly. Accordingly, this material is inappropriate for a pressure sensor. In the case of nano material-based devices, in view of properties of nano materials, it is difficult to obtain reproducibility.

Accordingly, there is a need to develop a pressure sensor that has excellent controllable electrical properties so that it is usable/applicable in various fields including humanoid-based robots, smart vehicles, aerial applications, simulation, process control, human being-friendly IT, fingerprint-recognition systems, bio-monitoring smart sensors, or the like, and that has excellent mechanical flexibility and stability.

SUMMARY

One or more exemplary embodiments include a pressure sensor including: a bottom substrate; a top substrate located on the bottom substrate and spaced apart from at least a portion of the bottom substrate; and an electronic sheet formed on at least a portion of the bottom substrate or at least a portion of a surface of the top substrate facing the bottom substrate, or a first electronic sheet formed on at least a portion of the bottom substrate and a second electronic sheet formed on at least a portion of a surface of the top substrate facing the bottom substrate; wherein the electronic sheet includes a graphitic material and a phage binding to the graphitic material, and the binding is made between a peptide displayed on a coat protein or a fragment thereof of the phage and the graphitic material.

One or more exemplary embodiments include a wearable device for measuring bio-information, the wearable device including the pressure sensor.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
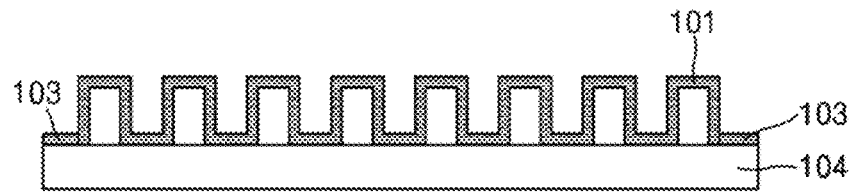
FIG. 1A-1C illustrate examples of a patterned bottom substrate of a pressure sensor according to an exemplary embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the exemplary embodiments are merely described below, by referring to the figures, to explain aspects of the present description. Expressions such as "at least one of," when preceding a list of elements, modify the entire list of elements and do not modify the individual elements of the list.

An aspect provides a pressure sensor including: a bottom substrate; a top substrate located on the bottom substrate and spaced apart from at least a portion of the bottom substrate; and an electronic sheet formed on at least a portion of the bottom substrate or at least a portion of a surface of the top substrate facing the bottom substrate, or a first electronic sheet formed on at least a portion of the bottom substrate and a second electronic sheet formed on at least a portion of a surface of the top substrate facing the bottom substrate; wherein the electronic sheet includes a graphitic material and a phage binding to the graphitic material, and the binding is made between a peptide displayed on a coat protein or a fragment thereof of the phage and the graphitic material.

The term "pressure sensor" used herein may be interchangeably used with "touch sensor" or "tactile sensor," and refers to an apparatus, tool, or device that detects given force, contact, pressure, tactus, or touch, and converts them into signals (for example, an electric signal). In some embodiments, the pressure sensor may be a flexible pressure sensor, and may be an integrated or miniaturized pressure sensor having a thickness of less than 1 mm. In some embodiments, the pressure sensor may have excellent controllable electrical properties, mechanical flexibility, and stability, and due to these properties, the pressure sensor may be used in humanoid robots, touch displays, bio-information measuring wearable devices, smart vehicles, aerial applications, simulation, process control, human-friendly IT, fingerprint recognition systems, or bio-monitoring smart sensors.

The term "sheet" used herein refers to a material having a certain width and a certain thickness, and for example, may include a film, a web, a membrane, or a complex structure thereof.

The term "graphitic material" used herein refers to a material having a surface with a hexagonal arrangement of carbon atoms, i.e., a graphitic surface, and may include any material having a graphitic surface, regardless of physical, chemical or structural properties. Examples thereof are a graphene sheet, a highly oriented pyrolytic graphite (HOPG) sheet, a graphene oxide, a reduced graphene oxide, a carbon nanotube such as a single-walled carbon nanotube, a double-walled carbon nanotube, and a multi-walled carbon nanotube, and fullerene. The graphitic material may be metallic, semi-conductive, or a hybrid thereof. For example, the graphitic material may be a combination of a graphene sheet and a single-walled carbon nanotube.

Figure 1B:
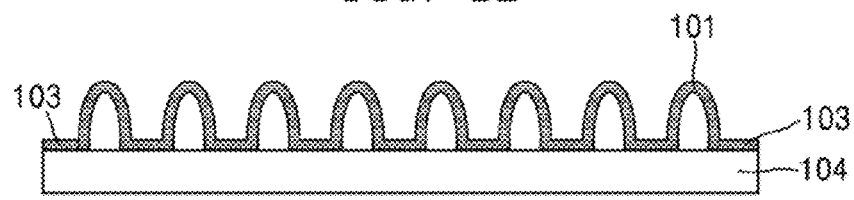
Figure 1C:
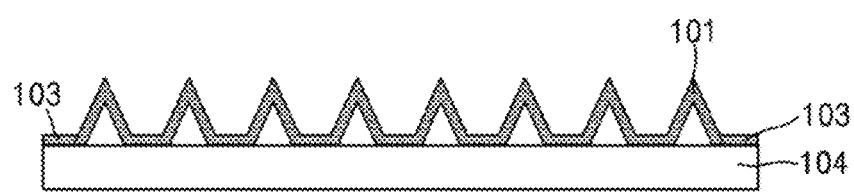
Figure 2A:
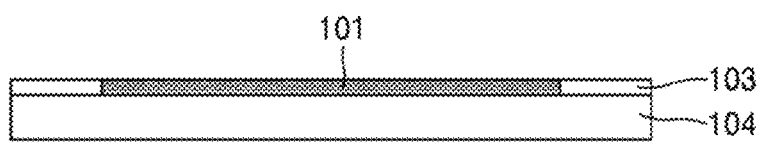
FIG. 2A-2C illustrate examples of a bottom substrate of a pressure sensor according to an exemplary embodiment.
Figure 2B:
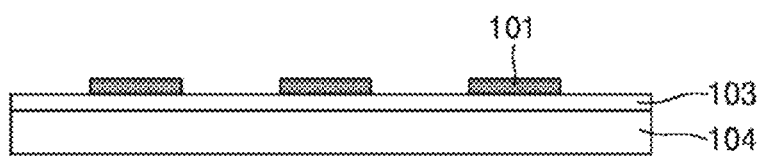
Figure 2C:
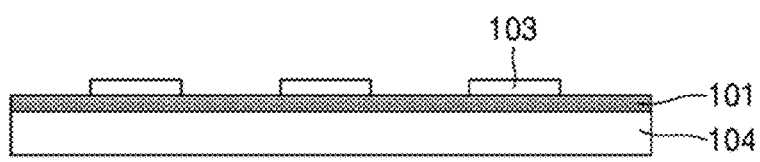
Figure 3A:
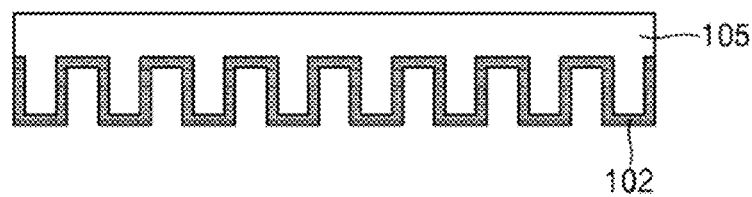
FIG. 3A-3C illustrate examples of a patterned top substrate of a pressure sensor according to an exemplary embodiment.
Figure 3B:
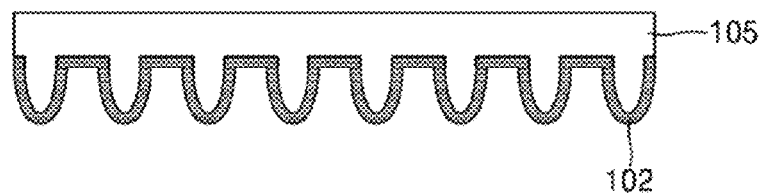
Figure 3C:
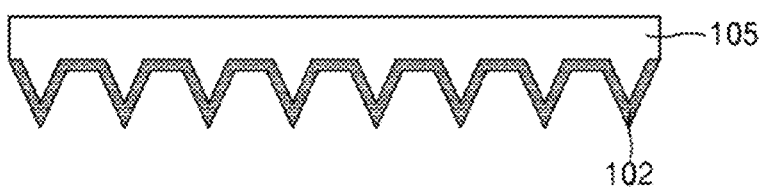

Referring to FIGS. 1 to 3, a bottom substrate 104 with a first electronic sheet 101 that has been transferred thereonto, or a top substrate 105 with a second electronic sheet 102 that that has been transferred thereonto may have a pattern. For example, the bottom substrate 104 or the top substrate 105 may have a patterned surface having a convex portion and a concave portion, and the convex portion may have a triangular, tetragonal, or circular cross-section. Also, the pressure sensor may further include an electrically connected to the electronic sheet 101, 102. In some embodiments, an electrode 103 may be electrically connected to at least one of the first electronic sheet 101 and the second electronic sheet 102, and may be patterned on the bottom substrate 104 or the top substrate 105. For example, the first electronic sheet 101 may be patterned and transferred between patterns of the electrode 103 on the bottom substrate 104. In some embodiments, the electrode 103 is transferred on the bottom substrate 104, and the first electronic sheet 101 is patterned and transferred on the electrode 103. In some embodiments, the first electronic sheet 101 is transferred on the bottom substrate 104, and the electrode 103 is patterned and transferred on the first electronic sheet 101. The second electronic sheet 102 and the electrode 103 may be disposed on the top substrate 105 in the same manner as described above.

In some embodiments, the pressure sensor may include a conductive material layer formed on the bottom substrate 104, or on at least a portion of a surface of the top substrate 105 facing the bottom substrate 104. For example, when an electronic sheet is formed on at least a portion of a surface of the top substrate 105 facing the bottom substrate 104, a conductive material layer may be formed on the bottom substrate 104, or when an electronic sheet is formed on the bottom substrate 104, a conductive material layer may be formed on at least a portion of a surface of the top substrate 105 facing the bottom substrate 104. The conductive material layer may include a conductive material, and examples thereof will be described below.

Each of the top substrate 105 and the bottom substrate 104 may be a flexible substrate, for example, a transparent flexible substrate. Each of the top substrate 105 and the bottom substrate 104 may be, for example, a substrate manufactured using polydimethylsiloxane (PDMS), polyethersulfone (PES), poly(3,4-ethylenedioxythiophene), poly(styrenesulfonate), polyimide, polyurethane, polyester, perfluoropolyether (PFPE), polycarbonate, or a combination of the forgoing polymers.

A material for the electrode 103 may include a conductive material, for example, silver, silver epoxy, palladium, copper, aluminum, gold, titanium, palladium, chromium, nickel, platinum, silver/silver chloride, silver/silver ion, or mercury/mercury oxide. In some embodiments, a conductive polymer may be used to form the electrode 103 due to its flexibility and ease of coating. In some embodiments, a conductive polymer may be used to form the electrode 103 due to its flexibility and ease of coating. An example of such a conductive polymer is poly(3,4-ethylenedioxythiophene) polystyrene sulfonate (PEDOT:PSS).

Figure 4:
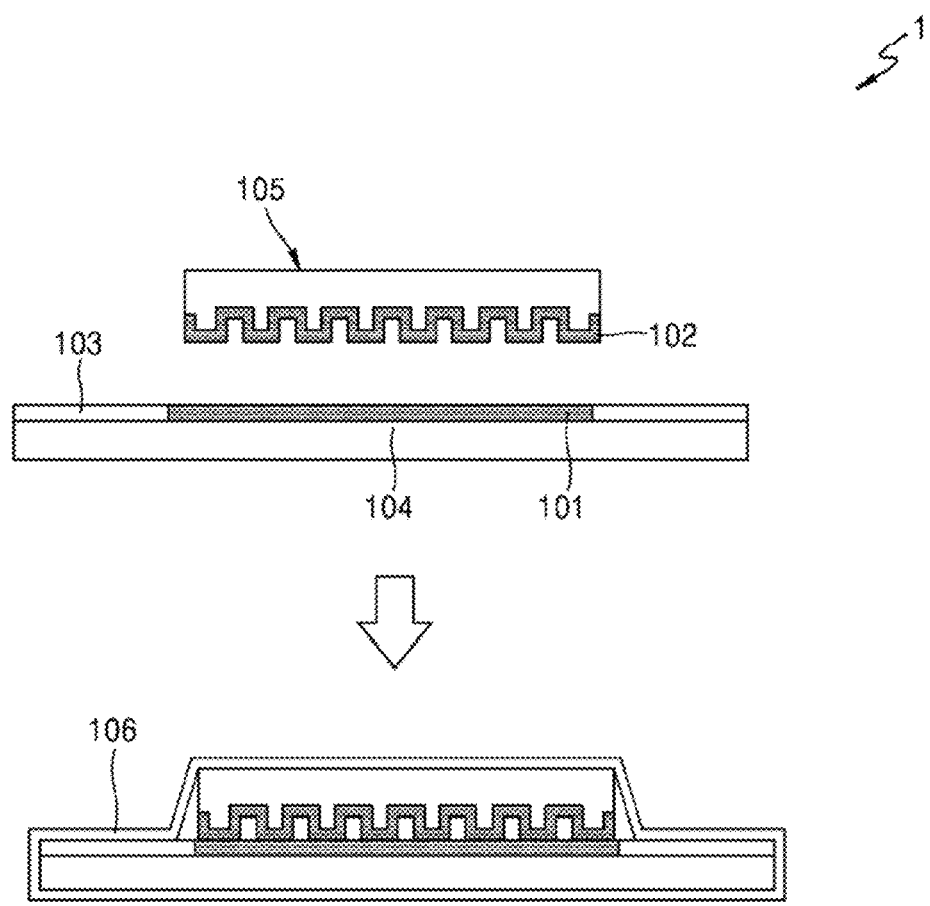
FIG. 4 illustrates a pressure sensor according to an exemplary embodiment.
Figure 5A:
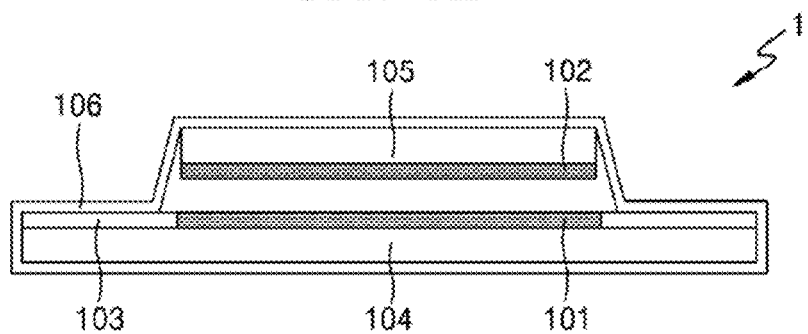
FIG. 5A-5D illustrate examples of a pressure sensor according to another exemplary embodiment.
Figure 5B:
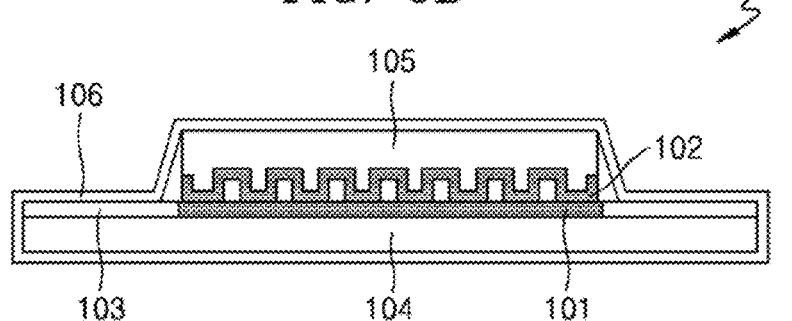
Figure 5C:
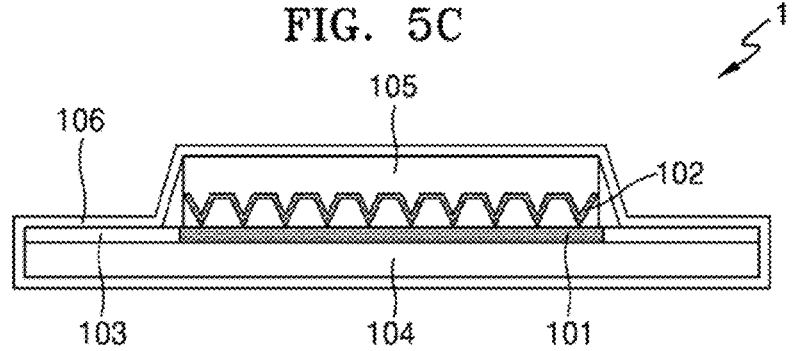
Figure 5D:
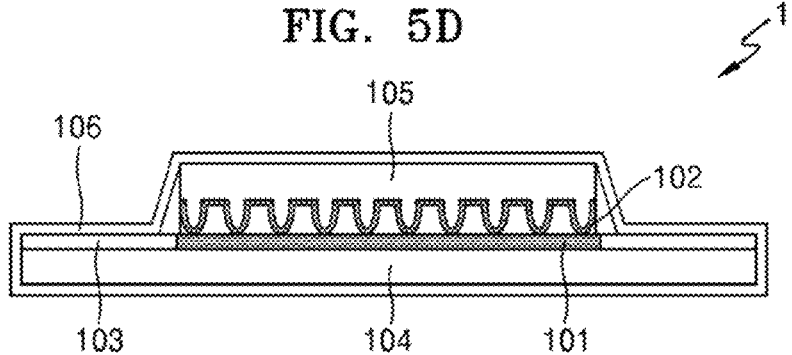
Figure 6A:
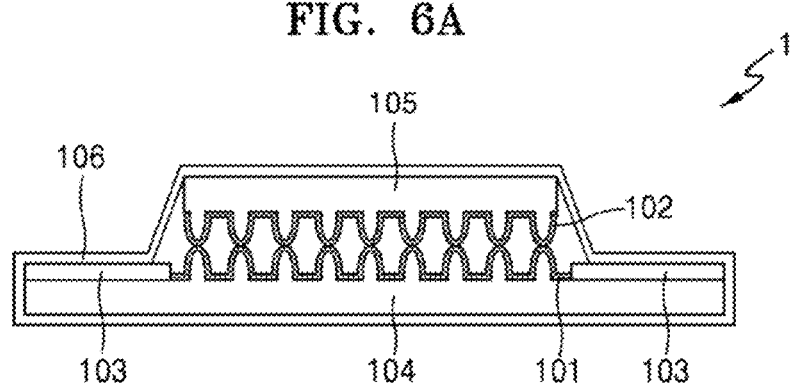
FIG. 6A-6D illustrate examples of a pressure sensor according to another exemplary embodiment.
Figure 6B:
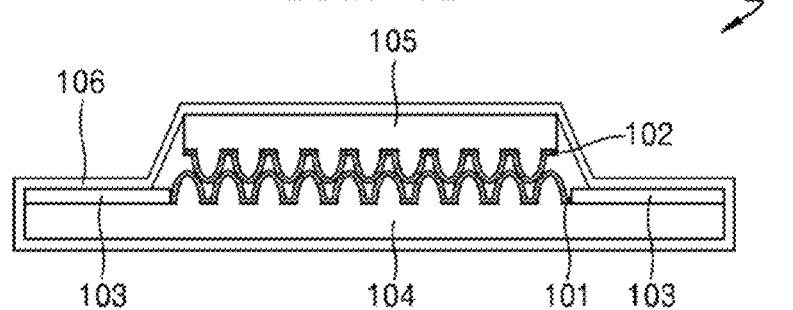
Figure 6C:
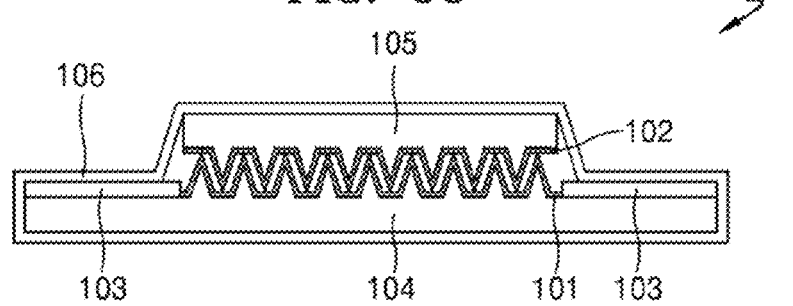
Figure 6D:
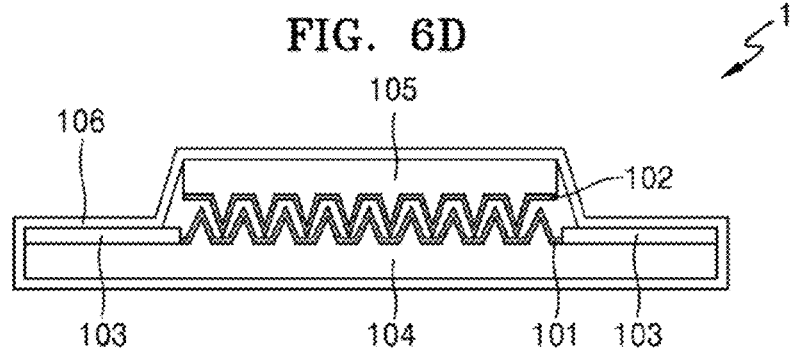

Referring to FIGS. 4 and 5, at least a portion of the first electronic sheet 101 may contact at least a portion of the second electronic sheet 102, or at least a portion of the second electronic sheet 102 may contact at least a portion of the first electronic sheet 101. For the contact, the lower substrate 104 with the first electronic sheet 101 transferred thereon, or the top substrate 105 with the second electronic sheet 102 transferred thereon may be patterned as described above. In some embodiments, the pressure sensor may further include a cover 106 located on a surface of the bottom substrate 104 or the top substrate 105 being opposite to where the first and second electronic sheets 101 and 102 are formed. The cover 106 may protect or house the pressure sensor, and may be integrally formed with the lower substrate 104 or the top substrate 105.

Referring to FIG. 6, at least a portion of the first electronic sheet 101 formed on a convex portion of the lower substrate 104 may contact at least a portion of the second electronic sheet 102 formed on a convex portion or concave portion of the top substrate 105. In some embodiments, at least a portion of the second electronic sheet 102 formed on a convex portion of the top substrate 105 may contact at least a portion of the first electronic sheet 101 formed on a convex portion or concave portion of the lower substrate 104. For the contact, the bottom substrate 104 or the top substrate 105 may be patterned as described above. The contact may occur, for example, between the longest convex portions of two substrates, between side surfaces of convex portions of two substrates, or between the longest convex portion of a substrate and a concave portion of the other substrate. Due to the contact according to an embodiment, the pressure sensor may have high sensitivity and may quickly respond to even shear force.

Figure 7A:
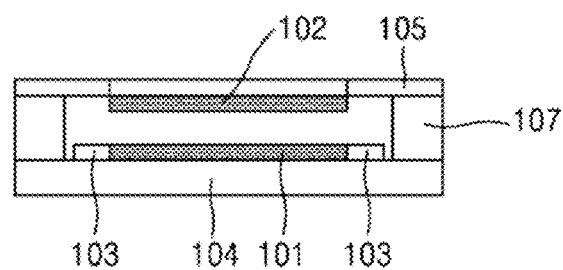
FIG. 7A-7B illustrate a pressure sensor according to an exemplary embodiment, including an intermediate insulating structure or an intermediate insulating layer.
Figure 7B:
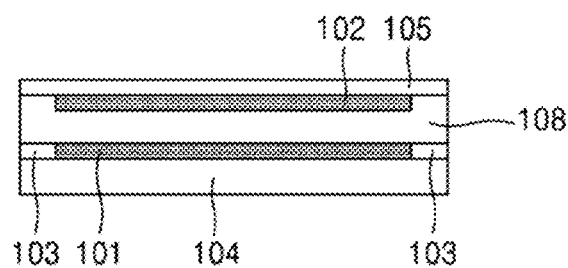

Referring to FIG. 7, the pressure sensor may further include an intermediate insulating structure 107 or an intermediate insulating layer 108 to space the lower substrate 104 from the top substrate 105. For example, the lower substrate 104 and the top substrate 105 may be spaced apart from each other by a certain distance with the intermediate insulating structure 107 or the intermediate insulating layer 108 therebetween. The height of the intermediate insulating structure 107 or intermediate insulating layer 108 may be adjusted to be greater than that of the electrode 103 or the first electronic sheet 101 formed on the bottom substrate 104.

Pressure applied to the lower substrate 104, the top substrate 105, or the cover 106 may change a contact area, contact distance or a conductive network density between the first electronic sheet 101 and the second electronic sheet 102. Due to the applied pressure, the first electronic sheet 101 and the second electronic sheet 102, which have been spaced apart from each other, may be brought into contact each other, or in the case in which the first electronic sheet 101 and the second electronic sheet 102 have partly contacted each other, the contact area thereof may increase. Due to the applied pressure, a conductive network of the first electronic sheet 101 may contact a conductive network of the second electronic sheet 102 more. For example, when a convex portion of the lower substrate 104 or the top substrate 105 has a tetragonal cross-section, the applied pressure may not lead to an increase in the contact area between the first and second electronic sheets 101 and 102, but their contact distance may be decrease, and their conductive networks may contact each other to a greater degree, resulting in a wider pressure driving range. For example, when a convex portion of the lower substrate 104 or the top substrate 105 has a pyramid-shape cross-section, the applied pressure may lead to an increase in the contact area and the conductive network contact between the first and second electronic sheets 101 and 102, resulting in a higher sensitivity. When the contact area, contact distance or the conductive network density changes, the resistance or current of a sensor may change, allowing pressure applied to the sensor to be detectable.

In some embodiments, the pressure sensor may measure applied pressure by measuring capacitance. For example, in the case of a pressure sensor including a bottom substrate and a top substrate that are spaced apart from each other without electric contact by an intermediate insulating structure or an intermediate insulating layer, when pressure is applied, capacitance of the pressure sensor changes, and by measuring the change in capacitance, the applied pressure is measured.

In some embodiments, the pressure sensor may include a processor (not shown) that measures a signal (for example, an electric signal) corresponding to applied pressure, or obtains information about, for example, applied pressure. The processor may obtain information about force or pressure (for example, intensity of force, direction of force, or how many times force is applied) by measuring varying resistance or current. The information may be converted into a certain signal (for example, an electrical signal), which is then displayed, or may be provided to a separate device connected to the pressure sensor so as to allow the separate device to perform a target operation. Accordingly, the processor may include an electronic device that converts a measured value into a display value, a display showing results, or one or more control interfaces. In some embodiments, through an external measuring device (not shown) connected via an electrode, the pressure sensor may perform the same operation as described in connection with the processor.

Figure 8:
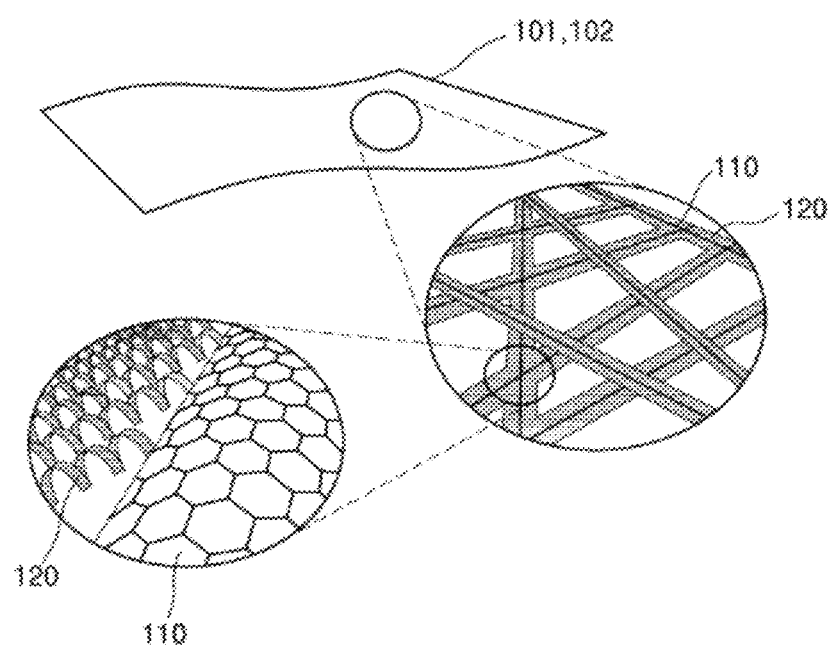
FIG. 8 illustrates a hybrid electronic sheet of a pressure sensor according to an exemplary embodiment.

Referring to FIG. 8, each of the first and second electronic sheets 101 and 102 may have an area of, for example, 0.0001 to 1000 $cm^2$, 0.0001 to 100 $cm^2$, or 1 to 20 cm2, and a thickness of, for example, 20 to 2000 nm, 40 to 1500 nm, 40 to 1000 nm, 60 to 500 nm, or 80 to 200 nm. In some embodiments, an internal structure of each of the first and second electronic sheets 101 and 102 including a graphitic material 110 and a phage 120 may have a percolated network structure. The term "percolated network" used herein refers to a lattice structure consisting of random conductive or non-conductive linkages.

Another aspect provides a method of preparing an electronic sheet including: preparing a colloid material including a graphitic material; adding a phage, which displays a peptide having a binding ability to the graphitic material on its coat protein or a fragment thereof, to a solution so as to prepare a phage solution; mixing the colloid material and the phage solution so as to prepare a mixture; and dialyzing the mixture using a membrane so as to form an electronic sheet in a solution.

In preparing the colloid material, the colloid material may be an aqueous solution, in which graphitic materials are dispersed or dissolved. The colloid material may be prepared by stabilizing the graphitic material in a surfactant-containing solution.

The surfactant may include a surfactant which is biocompatible with biomaterials such as a peptide or a phage. Examples thereof are sodium dodecyl sulfate (SDS), sodium deoxycholate (DOC), Nonidet P-40, Triton X-100, and Tween 20®.

In preparing the phage solution, the method of preparing the phage is the same as described above. In some embodiments, the prepared phage may be added to an appropriate solution, for example, distilled water, phosphate-buffered saline (PBS), or Tris-buffered saline (TBS), and the solution may have a pH of 5 to 8.

In an exemplary embodiment, when a graphene sheet is used as the graphitic material, a two-dimensional structure of the graphene sheet may provide a large contact area of constituent materials, compared to a material of one-dimensional structure. Therefore, it is possible to realize a large hybrid electronic sheet.

In an exemplary embodiment, when a combination of a graphene sheet and a single-walled carbon nanotube is used as the graphitic material, the concentration of the graphene sheet needs not to be high, which is necessary for when a graphene sheet is used alone, while retaining the advantage of the two-dimensional structure of the graphene sheet.

In an exemplary embodiment, when the graphene sheet is combined with the single-walled carbon nanotube, the size and thickness of the resultant sheet increase and the effective area of a nanoelectrode per unit area increases.

In the dialyzing to form the electronic sheet, a membrane tube containing the mixture may be dialyzed against a dialysis solution, or the mixture may be dialyzed by using a membrane in itself. The membrane may include a semipermeable film or any structure that allows a mixture, such as a material, to permeate therethrough. For example, the dialyzing to form the electronic sheet may be dialyzing in an ion-added solution. A concentration of ions included in the dialysis solution may be in a range of 0 or more to less than 10 mM. The ion concentration may be controllable by adding a monovalent electrolyte to the dialysis solution, for example, 0.1 mM NaCl to triple distilled water used for dialysis.

In some embodiments, the dialysis solution may be distilled water, triple distilled water (resistance>18 Mohm cm), PBS, or TBS in terms of stability with the phage.

In forming the electronic sheet by dialysis, the dialysis may be performed for about 5 to 60 hours, about 10 to 50 hours, or about 15 to 40 hours. After the dialysis, a thin electronic sheet may be formed along the surface of the membrane tube.

In some embodiments, the method of preparing the electronic sheet may further include, after forming the electronic sheet by dialysis, separating the formed electronic sheet from the membrane in an aqueous solution. The separation may be accomplished, for example, by twisting the membrane tube used for the dialysis to separate the electronic sheet formed along the membrane. A freestanding electronic sheet may be obtained by controlling a membrane clip in an aqueous solution.

In some embodiments, the method of preparing the electronic sheet may further include transferring the electronic sheet formed in the aqueous solution with a suitable substrate or mask according to its purpose. The substrate or mask may be made of a metal, a semiconductor, an insulator, a polymer, an elastomer, etc. For example, a flexible electronic device may be prepared by transferring the electronic sheet with a flexible polymer substrate. In some embodiments, this process is to form patterns on the electronic sheet by transferring the separated electronic sheet with a patterned substrate or mask. For example, when a patterned stencil mask is used, a pattern is formed on the electronic sheet when the mask is detached after the electronic sheet is completely dried. By this process, a device may be realized on a flexible electronic sheet without additional physical or chemical etching.

In preparing the mixture, a mixing ratio of the colloidal graphitic material and the phage solution may be controlled by those skilled in the art, depending on use of the electronic sheet. That is, the mixing ratio may be controlled depending on the desired properties of the electronic sheet, such as electrical conductivity, electrical conductive properties, electrochemical charging current, hydrophilicity, etc. For example, the molar ratio of the colloidal graphitic material and the phage solution may be controlled in terms of structural stability of the electronic sheet, formation of the electronic sheet with a large area, and electrical resistance of the electronic sheet. The molar ratio of the colloidal graphitic material and the phage solution may be in a range of 30:1 to 1:30, in a range of 20:1 to 1:20, in a range of 15:1 to 1:15, in a range of 10:1 to 1:10, or in a range of 8:1 to 1:8, for example, 20:1, 10:1, 4:1, 1:4, or 1:8.

In some embodiments, a resistance value of the electronic sheet may be dependent on the molar ratio of the colloidal graphitic material and the phage solution. Accordingly, by controlling the molar ratio, the numbers of the graphitic material and the phage included in the electronic sheet are controlled and thus, a resistance value of the electronic sheet is controlled. For example, a ratio of the number of graphitic material to the number of phages included in the electronic sheet in the first electronic sheet or the second electronic sheet may be in a range of 1:10 to 10:1, 1:8 to 8:1, 1:4 to 4:1, or 1:2 to 2:1.

In some embodiments, by controlling the molar ratio or the number ratio, a resistance value of the first electronic sheet may be equal to or greater than a resistance value of the second electronic sheet. When the resistance value of the first electronic sheet is equal to or greater than the resistance value of the second electronic sheet, a driving range of the pressure sensor may be widened compared to when the resistance value of the first electronic sheet is less than the resistance value of the second electronic sheet. In some embodiments, the resistance value of the first electronic sheet may be less than the resistance value of the second electronic sheet. When the resistance value of the first electronic sheet is less than the resistance value of the second electronic sheet, sensitivity of the pressure sensor may be higher than when the resistance value of the first electronic sheet is equal to or greater than the resistance value of the second electronic sheet. The sensitivity of the pressure sensor indicates a minimum level of pressure detectable by a sensor. An increased or high sensitivity means that the level of pressure detectable is decreased or low. The driving range of the pressure sensor may indicate a range of pressure detectable by a sensor, and an increased or wide driving range of the pressure sensor means that the range of pressure detectable increases or widens. When sensitivity of the pressure sensor is high, due to high pressure applied to a sensor, the sensor may have a saturated response degree, thereby having a narrow pressure driving range. When the driving range of the pressure sensor is wide, a response degree of the sensor with respect to applied pressure may less change. Accordingly, even at a high level of pressure, the sensor may measure change in pressure without saturation.

In an exemplary embodiment, the method of preparing the electronic sheet enables the manufacture of a nano structure in which a graphitic material and a phage are homogeneously dispersed, and also the manufacture of a large-area flexible electronic sheet having a thickness of 400 nm or less and an area having tens square centimeter.

In an exemplary embodiment, the method of preparing the electronic sheet may allow an electronic sheet to be transferred onto various substrates without chemical etching or use of an additional carrier material layer.

In an exemplary embodiment, the method of preparing the electronic sheet may provide ease of patterning using a substrate or a mask.

A peptide binding to the graphitic material may be a material capable of binding to the graphitic material in a nondestructive manner. The peptide may be selected from peptide libraries, for example, by a phage display technique. Through the phage display technique, the peptide may be genetically linked to, inserted into, or substituted for the coat protein of the phage, resulting in display of the protein on the exterior of phage, in which the peptide may be encoded by genetic information in the virion. Variants of the protein may be selected and screened by the displayed protein and DNA encoding the same, and this method is called "biopanning". Briefly, biopanning is carried out by incubating the pool of phage-displayed variants with a target (e.g., graphitic material) that has been immobilized, washing away unbound phage, and eluting specifically bound phage by disrupting the binding interactions between the phage and the target. A portion of the eluted phage is set aside for DNA sequencing and peptide identification, and the remainder is amplified in vivo to prepare a sub-library for the next round. Then, this procedure is repeated.

The term "phage" or "bacteriophage" is used interchangeably, and refers to a virus that infects bacteria and replicates within the bacteria. The phage or bacteriophage may be used to display a peptide which selectively or specifically binds to a graphitic material or volatile organic compound. The phage may be genetically engineered to display the peptide capable of binding to the graphitic material on a coat protein of the phage or a fragment thereof. As used herein, the term "genetic engineering" or "genetically engineered" means introduction of one or more genetic modifications into the phage in order to display the peptide capable of binding to the graphitic material on the coat protein of the phage or the fragment thereof, or a phage prepared thereby. The genetic modifications include introduction of a foreign gene encoding the peptide. The phage may be a filamentous phage, for example, M13 phage, F1 phage, Fd phage, If1 phage, Ike phage, Zj/Z phage, Ff phage, Xf phage, Pf1 phage, or Pf3 phage.

The term "phage display" or "phage with a peptide displayed thereon" used herein refers to a display of a functional foreign peptide or protein on the surface of a phage or phagemid particle. The surface of the phage may refer to a coat protein of the phage or a fragment thereof.

The functional foreign peptide may be present as being linked to the N-terminus of the coat protein of the phage, or as being inserted into a coat protein. The phage may be a phage in which the C-terminus of a functional foreign peptide is linked to the N-terminus of the coat protein of the phage, or the peptide is inserted between consecutive amino acid sequences of the coat protein of the phage or replaced for a part of the consecutive amino acid sequences of the coat protein. The positions in the amino acid sequence of the coat protein, at which the peptide is inserted or replaced, may be positions of 1 to 5, positions of 1 to 40, positions of 1 to 30, positions of 1 to 20, position of 1 to 10, positions of 2 to 8, positions of 2 to 4, positions of 2 to 3, positions of 3 to 4, or a position of 2, from the N-terminus of the coat protein. In some embodiments, the coat protein may be p3, p6, p8 or p9.

The peptide having a binding affinity specifically to the graphitic material may be a peptide or a peptide set including one or more selected from the group consisting of amino acid sequences of $X_2SX_1AAX_2X_3P$(SEQ ID NO. 1), $X_2X_2PX_3X_2AX_3P$(SEQ ID NO. 2), $SX_1AAX_2X_3P$(SEQ ID NO. 3), and $X_2PX_3X_2AX_3P$(SEQ ID NO. 4). In some embodiments, the peptide or peptide set may include one or more selected from the group consisting of amino acid sequences of SEQ ID NOS. 5 to 8. Consecutive amino acid sequences of a coat protein of a phage may be linked to the N-terminus or C-terminus of the amino acid sequence of the peptide or peptide set. Therefore, for example, the peptide or peptide set may have an amino acid sequence having a length of 5 to 60, 7 to 55, 7 to 40, 7 to 30, 7 to 20, or 7 to 10 amino acids.

The peptide may have a conservative substitution of a known peptide. The peptide may have a conservative substitution of a known peptide. The term "conservative substitution" used herein denotes replacement of a first amino acid residue with a second different amino acid residue without changing biophysical properties of a protein or a peptide. Here, the first and second amino acid residues mean those having side chains having similar biophysical properties. The similar biophysical properties may include an ability to donate or accept hydrophobicity, charge, polarity, or hydrogen bonding. Examples of the conservative substitution are within the groups of basic amino acids (arginine, lysine, and histidine), acidic amino acids (glutamic acid and aspartic acid), polar amino acids (glutamine and asparagine), hydrophobic amino acids (leucine, isoleucine, valine and methionine), hydrophilic amino acids (aspartic acid, glutamic acid, asparagine and glutamine), aromatic amino acids (phenylalanine, tryptophan, tyrosine and histidine), and small amino acids (glycine, alanine, serine and threonine). Amino acid substitutions that do not generally alter specific activity are known in the art. For example, in the peptide, $X_1$ may be W, Y, F, or H, $X_2$ may be D, E, N, or Q, and $X_3$ may be I, L, or V.

For example, the C-terminus of any one peptide of SEQ ID NO. 1 to SEQ ID NO. 8 may be linked to the body of M13 phage, that is, not to the tip of the phage, but to the N-terminus of p8 (SEQ ID NO. 19) having a length of 50 amino acids, which is present on the body in a longitudinal direction. In some embodiments, for example, any one peptide of SEQ ID NO. 1 to SEQ ID NO. 8 may be replaced for the positions of 2 to 4 (e.g., EGD), the positions of 2 and 3 or 3 and 4, or the position of 2 in the amino acid sequence of the coat protein p8 of M13 phage.

In an exemplary embodiment, a phage that displays a peptide having a binding affinity to a graphitic material specifically bind to the graphitic material, and thus additional functionalities may be provided by a non-destructive method that does not cause damage to properties of the graphitic material. In a case in which the peptide is displayed on the coat protein of the filamentous phage, a contact area with the graphitic material is large enough to provide a stronger binding affinity.

In an exemplary embodiment, the phage may be arranged on the graphitic surface with directionality using the filamentous structure of the phage in itself. For example, the phage may be arranged in a row in a specific direction. In this case, the binding affinity of the peptide present on the coat protein of the phage for the graphitic surface is enhanced and the phage is arranged in a row. The phage arranged in a row may provide anisotropic functionality to the graphitic surface, which is distinguishable from isotropic or random functionalities which are available when peptide is used alone. In addition to the arrangement in a row, the phage may be arranged to form a structure having specific directionality, such as a layered (e.g., smectic), nematic, spiral or lattice structure. Accordingly, various functionalities may be provided onto the graphitic surface using the arrangement structures of the phage.

In some embodiments, the pressure sensor may be a pressure sensor for measuring blood pressure or a heart rate.

The blood pressure may be arterial pressure, capillary blood pressure, or venous pressure, and in general, the blood pressure may mean arterial pressure. The arterial pressure changes corresponding to cardiac impulse. The blood pressure may be measured in an invasive manner or a non-invasive manner. In an embodiment, the pressure sensor may be connected to a catheter to measure blood pressure. In an example of the invasive manner, a catheter is inserted into a blood vessel to measure blood pressure through a connector containing, for example, a Heparin isotonic sodium chloride solution. In some embodiments, the pressure sensor is connected to a front end of the catheter to measure blood pressure. In the non-invasive manner, in some embodiments, the pressure sensor may be located on a site where a pulse wave is measurable, for example, a soft skin site where the radial artery, the brachial artery, the carotid artery, the carotid vein, the femoral artery, the popliteal artery, the tibial artery, or the dorsal pedis artery runs. In some embodiments, the pressure sensor may measure blood pressure by detecting the pressure (e.g. blood pressure) delivered to a skin site located above the blood vessel when the heart pulses and the blood vessel shrinks or expands.

In some embodiments, the pressure sensor may measure a heart impulse or a heart rate by detecting a pulse occurring in a blood vessel or vein when the heart pulses and converting the pulse into an electric signal.

Another aspect provides a wearable device including a pressure sensor, the pressure sensor including: a bottom substrate; a top substrate located on the bottom substrate and spaced apart from at least a portion of the bottom substrate; and an electronic sheet formed on at least a portion of the bottom substrate or at least a portion of a surface of the top substrate facing the bottom substrate, or a first electronic sheet formed on at least a portion of the bottom substrate and a second electronic sheet formed on at least a portion of a surface of the top substrate facing the bottom substrate; wherein the electronic sheet includes a graphitic material and a phage binding to the graphitic material, and the binding is made between a peptide displayed on a coat protein or a fragment thereof of the phage and the graphitic material.

The pressure sensor is the same as described above.

The wearable device is used to measure bio-information, and the bio-information may include blood pressure or a heart rate. In an exemplary embodiment, the bio-information may be force or pressure generated by walking, and one or more pressure sensors may be mounted on the sole of a person's foot or footwear to measure the intensity or distribution degree of force caused by walking. Also, one or more pressure sensors may be mounted on a person's tooth or oral cavity to measure degree of force or distribution due to a tooth bite. Accordingly, in some embodiments, the wearable device may be a patch, a band, a watch, footwear, tooth attached device.

In some embodiments, the wearable device may further include a controller that logically communicates with the pressure sensor, and receives and processes signal data generated by the pressure sensor so as to output data associated with controlling the pressure sensor.

The pressure sensor of the wearable device may be controlled by the controller, which responds at certain time intervals or responds to a particular event (for example, a switch operation) and receives and processes bio-information detected by the pressure sensor.

In some embodiments, the wearable device may further include a memory that stores a processor for operation of a controller, and that temporally stores input/output data (for example, bio-information). The memory may store information (for example, blood pressure or heart rate) about electrical signals transmitted by the pressure sensor.

In some embodiments, the wearable device may further include a display unit that displays information processed by the controller or information stored by the memory. In some embodiments, the wearable device may further include a wireless communication unit that sends information processed by the controller or information stored by the memory to a person wearing the wearable device or other users (for example, a person located near the person wearing the wearable device, a trainer of athletes, a physician, a hospital, or the family of the person wearing the wearable device) all having a wireless communication system. For example the wireless communication unit may include a broadcasting receiving module, a mobile communication module, a wireless Internet module, or a near-distance communication module. Information detected by the pressure sensor may be sent to the person wearing the wearable device including the pressure sensor or other users through the wireless communication unit.

The pressure sensor has excellent controllable electric properties, and mechanical flexibility and stability, and accordingly, the pressure sensor is effectively used in the wearable device configured to measure bio-information (for example, blood pressure or heart rate).

Hereinafter, embodiments of the inventive concept will be described. However, the embodiments are presented herein for illustrative purpose only, and do not limit the scope of the inventive concept.

EXAMPLES: MANUFACTURE OF PRESSURE SENSOR AND ANALYSIS ON CHARACTERISTICS THEREOF

1. Manufacture of Pressure Sensor 1
(1) Preparation of Hybrid Electronic Sheet 1
(1.1) Preparation of Colloid Solution First, an aqueous solution was prepared by adding 2% w/v sodium cholate as a surfactant to distilled water, and a colloid solution was prepared by stabilizing single-walled carbon nanotubes with the sodium cholate by dialysis of carbon nanotubes (manufacturer: Nanointegris, SuperPure SWNTs, solution-type, concentration: 250 mg/ml) for 48 hours.

In this regard, assuming that an average length and an average diameter of the carbon nanotube (CNT) were 1 μm and 1.4 nm, respectively, the number of single-walled carbon nanotubes included in the colloid solution was calculated according to the following equation.

$$\text{Number of single-walled carbon nanotubes (number/mL)} = \text{concentration (μg/mL)} \times 3 \times 10^{11} \text{ CNT} \quad \text{[Equation 1]}$$

According to this Equation, the number of the single-walled carbon nanotube included in the colloid solution was $7.5 \times 10^{13}$/mL.

(1.2) Preparation of Phage Displaying Peptide Having Binding Ability to Graphitic Material As M13 phages having a strong binding affinity to the graphitic surface, an M13 phage (p8 GB#1) displaying a peptide DSWAADIP (SEQ ID NO. 5) having a strong binding affinity to the graphitic surface and an M13 phage (p8 GB#5) displaying a peptide DNPIQAVP (SEQ ID NO. 6) were prepared by the following method.

First, an M13HK vector was prepared using oligonucleotides of SEQ ID NOS. 10 and 11 for site-directed mutation of the 1381st base pair C of an M13KE vector (NEB, product #N0316S) (SEQ ID NO. 9) to G. The prepared M13HK vector was double-digested using restriction enzymes, BspHI (NEB, product #R0517S) and BamHI (NEB, product #R3136T), and dephosphorylated using antarctic phosphatase. The dephosphorylated vector was ligated to a double-digested DNA duplex by incubation at 16° C. overnight. A product is then purified and concentrated. Electrocompetent cells (XL-1 Blue, Stratagene) were transformed with 2 μl of a concentrated ligated vector solution by electroporation at 18 kV/cml. A total of five transformations were performed for the library construction. Then, the transformed cells were incubated for 60 minutes, and fractions of several transformants were plated onto agar plates containing x-gal/isopropyl-β-D-1-thiogalactopyranoside (IPTG)/tetracycline (Tet) to determine the diversity of the library. The remaining cells were amplified in a shaking incubator for 8 hours. Oligonucleotides of SEQ ID NOS. 12 and 13 were used in construction of the phage-display p8 peptide library.

The base sequences of the phage-display p8 peptide library constructed according to an exemplary embodiment had diversity of $4.8 \times 10^7$ pfu (plaque forming unit), and include approximately $1.3 \times 10^5$ copies of each sequence.

Then, a highly ordered pyrolytic graphite (HOPG) substrate (manufacturer: SPI product #439HP-AB) having a diameter of 1 cm was prepared. In this regard, the HOPG substrate was a HOPG substrate having a relatively large grain size of 100 μm or smaller. Previously, a carbon nanotube film surface damaged during its production process had been generally used as a graphitic surface, and thus it was difficult to identify peptides having high binding affinity. In order to solve this problem, HOPG as a material having a graphitic surface was detached from a substrate by using a tape immediately before use, thereby obtaining a fresh surface, so as to minimize the occurrence of defects caused by, for example, oxidation. Subsequently, the phage display p8 peptide library of $4.8 \times 10^{10}$ pfu ($4.8 \times 10^7$ diversities, 1000 copies per each sequence), prepared as described above, was prepared in 100 μL of tris-buffered saline (TBS) and conjugated with the HOPG surface for 1 hour in a shaking incubator at 100 rpm. 1 hour later, the solution was removed and the surface was washed 10 times in TBS. The washed HOPG surface was reacted with Tris-HCl of pH 2.2 as an acidic buffer for 8 minutes to elute peptides reacting non-selectively, and the remaining phage was eluted with an XL-1 blue *E. coli* culture in mid-log phase for 30 minutes. A portion of the eluted culture was set aside for DNA sequencing and peptide identification, and the remainder was amplified to prepare a sub-library for the next round. The above procedure was repeated using the prepared sub-library. Meanwhile, the left plaque was subjected to DNA sequencing to obtain the p8 peptide sequence, and the sequence was analyzed to obtain a phage (P8 GB#1) with DSWAADIP (SEQ ID NO: 5) displayed thereon and a phage (p8 GB#5) with DNPIQAVP(SEQ ID NO: 6) displayed thereon. Herein, DSWAADIP (SEQ ID NO: 5) and DNPIQAVP(SEQ ID NO: 6) were peptide sequences having a strong binding affinity to a graphitic material.

Also, regarding the binding between the phage and the graphitic material, it was considered that an aspartic acid (D), which is a first amino acid sequence from the N-termini of SEQ ID NOS. 5 and 6, does not affect the binding, and a phage with peptide sequences of SWAADIP(SEQ ID NO. 7) and NPIQAVP(SEQ ID NO. 8) displayed thereon was obtained to confirm its binding to a graphitic material.

(1.3) Preparation of Phage-Bound Hybrid Electronic Sheet

The colloid solution prepared above and a phage solution containing the M13 phage (p8 GB#1) having a strong binding force to the graphitic material were mixed at a molar ratio of 8:2.

Next, for dialysis, the mixture was added to a semipermeable dialysis membrane (SpectrumLab, MWCO 12,000 to 14,000, product #132 700) tube, and the membrane tube was dialyzed against triple distilled water. About 16 hours after the dialysis began, a thin electronic sheet was formed along the surface of the membrane tube. Next, the membrane tube was transferred to triple distilled water and the electronic sheet was detached by twisting the membrane of the membrane tube and then dried.

Figure 9:
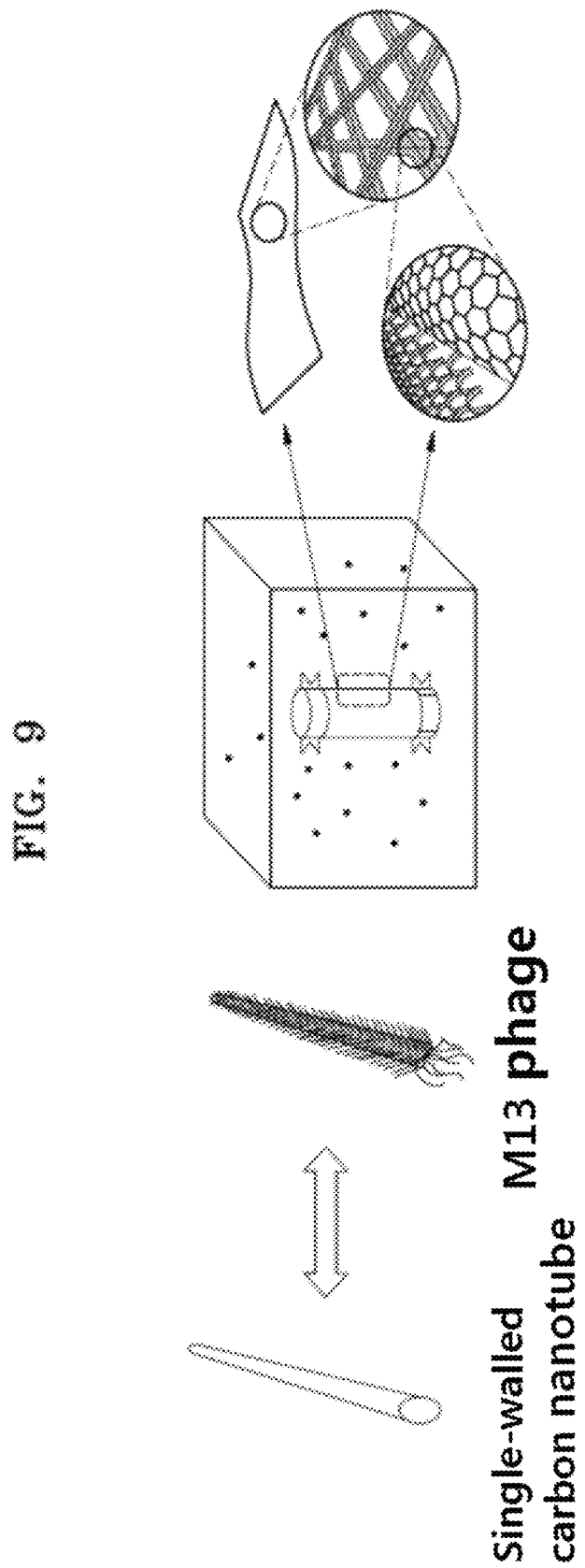
FIG. 9 illustrates how to manufacture a hybrid electronic sheet of a pressure sensor according to an exemplary embodiment.

FIG. 9 illustrates how to manufacture a hybrid electronic sheet of a pressure sensor according to an exemplary embodiment.

As shown in FIG. 9, it is seen that carbon nanotubes were dispersed or dissolved in the colloid material which was stabilized by adding it to the surfactant-containing solution. Single-walled carbon nanotube was bound with M13 phage finally to form a sheet having a percolated network structure of carbon nanotubes and M13 phage.

(2) Manufacture of Bottom Substrate of Pressure Sensor

A PDMS polymer substrate was used as a bottom substrate. Sylgard® 184 silicon elastomer and a Sylgard® 184 silicon elastomer curing agent were mixed at a ratio of 10:1, and then, a thickness of the result was adjusted by petri-dish spin coating, and curing was performed thereon in an oven at a temperature of 70° C. for about 6 hours. The cured PDMS film was cut to a desired size by using a knife for surgery. On the separated flexible polymer PDMS film, a Stencil mask was mounted, and then, a metal electrode (Pt) was placed thereon by sputtering. Between patterns of the metal electrode, the hybrid electronic sheet prepared according to Example 1.3 was transferred on by using a stencil mask having a size of 1.5×1.5 cm, and then dried in air for about 1 hour. The resultant dried substrate with the hybrid electronic sheet electrode transferred thereon was used as a bottom substrate for a flexible pressure device.

(3) Manufacture of Top Substrate of Pressure Sensor

A mould for a patterned polymer substrate for use as a top substrate was manufactured. First, SU-8 100 (manufactured by Microchem Company) was spin-coated on a silicon wafer at a rotational rate of 3000 rpm, and then, sequentially cured at a temperature of 60° C. for 30 minutes and then, at a temperature of 90° C. for 60 minutes, and then, ultraviolet (UV) light was irradiated thereto through a mask having a target pattern and a mask aligner. A target pattern thickness was adjusted by controlling the thickness of a SU-8 film. A width of a line pattern was designed to be in a range of 200 to 400 µm. After the irradiation of UV light, the result was cured at a temperature of 60° C. for about 1 minutes, and then, at a temperature of 90° C. for about 20 minutes, and then, the formed pattern was developed by using a developer dedicated for SU-8 only (manufactured by Microchem Company). The silicon wafer with a pattern thereon was used as a mould. In the case of a round mould, the line pattern formed as described above or a box pattern was formed by using photoresist, and then, an outer wall of a polymer was melted by using a polymer reflow method, thereby completing the manufacture of a round silicon mould. In the case of a pyramid-shape mould, a tetragonal concave pattern was formed on a silicon wafer by using a photoresist, and a portion of the silicon wafer corresponding to the tetragonal concave pattern that was not protected by the photoresist was etched by using a silicon etching solution (HF), thereby completing the manufacture of a pyramid-shape concave pattern.

Like the condition used to prepare the PDMS bottom substrate, Sylgard®184 silicon elastomer and a Sylgard® 184 silicon elastomer curing agent were mixed at a ratio of 10:1, and the mixture was spin-coated on the silicon wafer mould with a pattern thereon while adjusting a thickness of the formed film, and curing was performed thereon in an oven at a temperature of 70° C. for about 6 hours. The cured PDMS film was carefully separated from the silicon wafer mould by using a knife for surgery, thereby completing manufacture of a patterned top substrate. A hybrid electronic sheet was transferred onto the patterned top substrate by using a stencil mask, and then dried in air for about 1 hour. The hybrid electronic sheet transferred on the patterned top substrate was washed with distilled water after the stencil mask was removed, and then, dried by using nitrogen gas.

Figure 10:
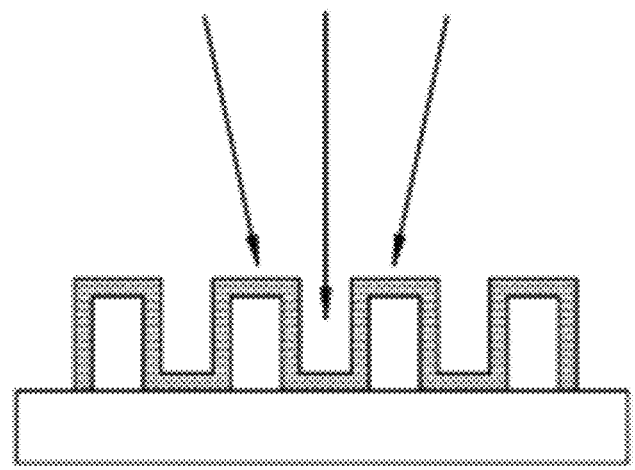
FIG. 10 illustrates a top substrate of a pressure sensor according to an exemplary embodiment with the hybrid electronic sheet transferred thereon.

FIG. 10 illustrates the top substrate of a pressure sensor according to an exemplary embodiment with the hybrid electronic sheet transferred thereon.

As shown in FIG. 10, the hybrid electronic sheet can be conformally formed even on a substrate having a step.

(4) Manufacture of Pressure Sensor

The top substrate and the bottom substrate, each having the dried hybrid electronic sheet coated thereon, were stacked on each other, and then, the result structure was packaged by using a sticky polymer material, thereby completing the manufacture of a flexible pressure device. For the packaging, a PDMS solution that had been prepared at a ratio of 10:1 like the condition used to manufacture the bottom substrate, was used in an appropriate amount for coating outside the stack structure of top/bottom PDMS substrate, and then, cured at a temperature of 80° C. for about 30 minutes. Also, instead of the PDMS solution, an epoxy curing agent/a polyacrylate polymer adhesive were used to contact the two PDMS polymer substrates.

The pressure sensor according to an exemplary embodiment may be a large-area flexible pressure sensor device having a thickness of 1 mm or less.

2. Analysis on Properties of Pressure Sensor (1) Analysis on Basic Properties

Performance of the manufactured pressure sensor was measured by using a 4156A precision semiconductor parameter analyzer manufactured by HP Company. Different pressures were applied to the manufactured pressure sensor and a voltage of −1V to +1V was applied to two electrodes to measure I-V (current vs. voltage) signals according to pressure, and results thereof are shown in FIGS. 11 and 12.

Figure 13:
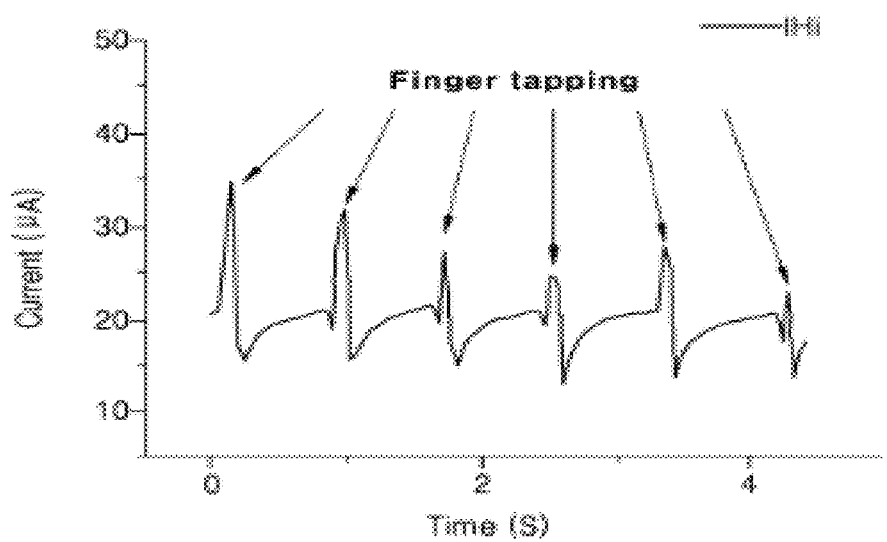
FIG. 13 illustrates a graph of change in current of the pressure sensor over time caused by force generated by the finger-tapping.

Also, whether the flexible pressure sensor promptly responds to a sudden change in pressure was confirmed as follows: a voltage of 2 V was applied to two electrodes and about 2 to 4 kPa of pressure was applied to the manufactured pressure sensor by tapping to measure real-time change in current by tapping, and results thereof are shown in FIG. 13.

Figure 11:
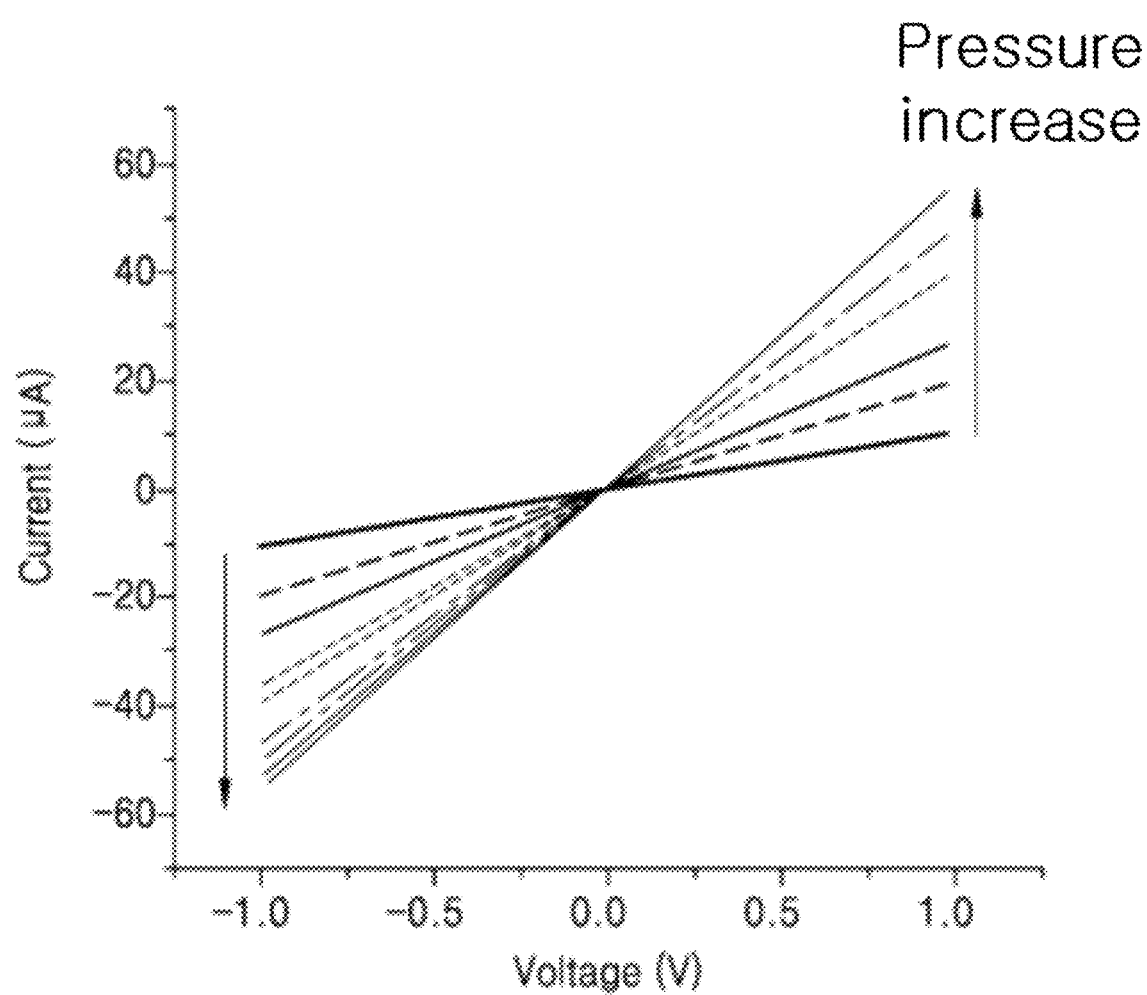
FIG. 11 is a graph of current when different levels of pressure are applied to a pressure sensor according to an exemplary embodiment.
Figure 12:
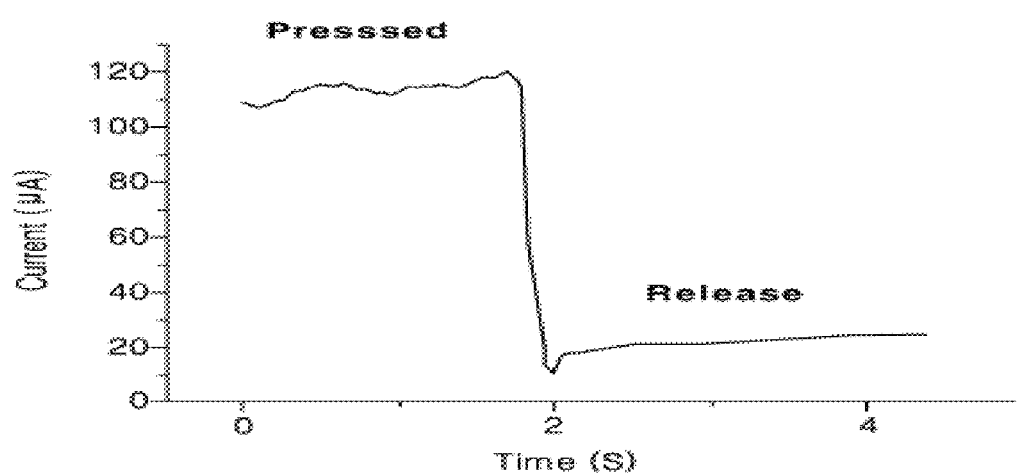
FIG. 12 is a graph of current when a pressure sensor according to an exemplary embodiment is pressed or released.

FIG. 11 is a graph of current when different levels of pressure are applied to a pressure sensor according to an exemplary embodiment.

Referring to FIG. 11, it is seen that a higher pressure leads to a higher current flowing through a pressure sensor. This result shows that when the pressure sensor is more pressed, a contact area between a top substrate and a bottom substrate, each having an electronic sheet transferred thereon, is widened and accordingly, the resistance occurring between two electrodes decreases and the current flowing therebetween increases.

FIG. 12 is a graph of current when a pressure sensor according to an exemplary embodiment is pressed or released.

Referring to FIG. 12, when the pressure sensor is pressed, resistance is low and accordingly, high current flows, and when the pressure sensor is released, the current of the released pressure sensor is dropped to a range of 200 to 300 ms. Also, in view of the constant current flowing in the pressure sensor, it is seen that according to pressure applied to the pressure sensor, a resistance value of a hybrid electronic sheet changes quickly and stably.

FIG. 13 illustrates a graph of change in current of the pressure sensor over time caused by force generated by the finger-tapping.

Referring to FIG. 13, when a sudden finger-tapping occurs, the current promptly increases and decreases, and the response speed of the flexible pressure sensor with respect to the finger-tapping is 50 ms or less.

(2) Analysis on Characteristics of Wearable Device

This experiment was performed to confirm whether the manufactured pressure device can be as a wearable device. A voltage of 2 V was applied between two electrodes, and flexible pressure devices were attached on the wrist where radial artery runs and the neck where carotid vein runs to measure change in blood pressure, and results thereof are shown in FIG. 14.

Figure 14:
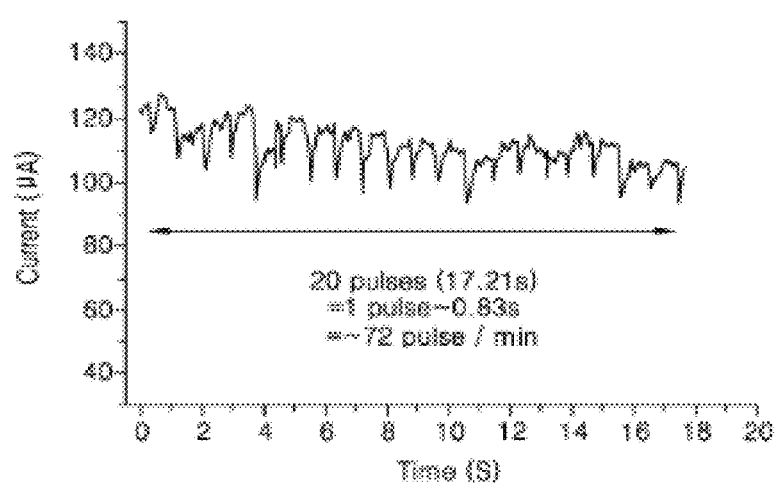
FIG. 14 illustrates a graph of current converted from a pulse of blood flow at radial artery measured by using a pressure sensor according to an exemplary embodiment.

FIG. 14 illustrates a graph of current converted from a pulse of blood flow at radial artery measured by using a pressure sensor according to an exemplary embodiment.

Referring to FIG. 14, in the case of radial artery of the wrist, 20 pulses were measured for about 17 seconds, and each of the pulses had a period of about 0.83 s. In general, an ordinary person has about 65 to 75 blood pressure pulses per minute. The graph shows about 72 pulses for one minute which was measured by using a pressure sensor according to an exemplary embodiment. This result shows that the pressure sensor according to an exemplary embodiment can be used in a wearable device measuring blood pressure worn on a curved wrist.

(3) Analysis on Responding Property

The manufactured pressure device was compared with a commercially available force sensitive resistor (FSR)-based pressure sensor to analyze a responding property thereof.

Figure 15:
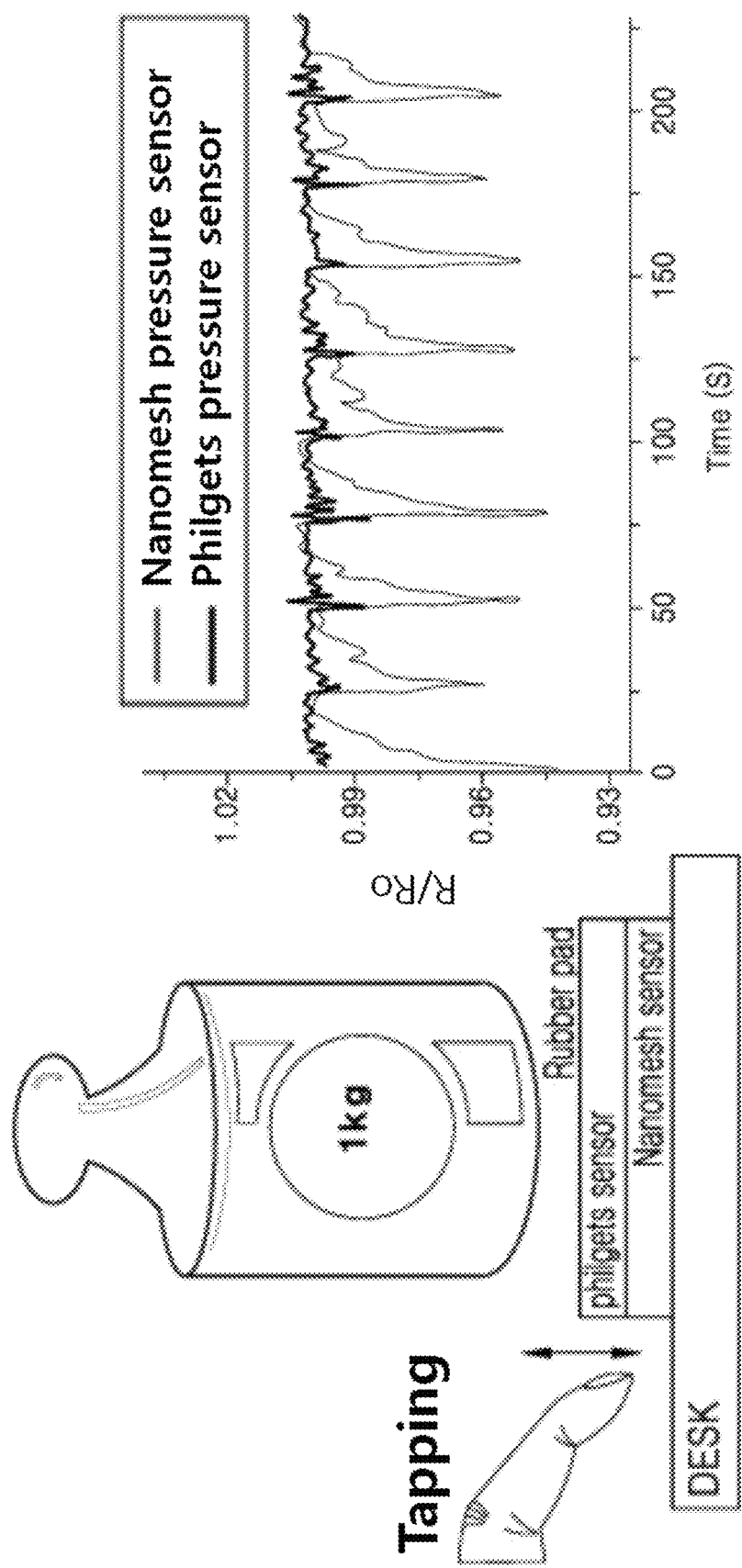
FIG. 15 illustrates a schematic diagram showing how an experiment was performed in which a pressure sensor according to an exemplary embodiment was compared with a commercially available Phidgets FSR sensor having a diameter of 10 mm, and a graph of a responding property of the two sensors with respect to vibration caused by finger-tapping on a desk.

Referring to FIG. 15, a hybrid electronic sheet-based flexible pressure device was stacked on a Philgets FSR sensor having a diameter of 10 mm, and then, a 1 kg (about 100 kPa) weight was placed on these two sensors. Then, a surrounding area thereof was tapped by using a finger and at this time, and the resistance of the sensors was measured. Results thereof are shown in FIG. 15.

FIG. 15 illustrates a schematic diagram showing how an experiment was performed in which a pressure sensor according to an exemplary embodiment was compared with a commercially available Phidgets FSR sensor having a diameter of 10 mm, and a graph of a responding property of the two sensors with respect to vibration caused by finger-tapping on a desk.

Referring to FIG. 15, the sensors commonly showed a decrease in resistance due to vibration caused by tapping in the same period. The decrease in resistance to micro vibration caused by finger-tapping the pressure sensor according to an exemplary embodiment was about 7 times as high as that of the FSR sensor, and accordingly, it is seen that the pressure sensor according to an exemplary embodiment is more sensitive to vibration than the FSR sensor. That is, it is seen that the pressure sensor manufactured using a hybrid electronic sheet including a highly conductive/functional carbon nanotube was a highly-sensitive flexible pressure sensor that responds to even small change in pressure compared to the metal/polymer-based commercially available FSR sensor.

3. Controlling Sensitivity of Pressure Sensor by Controlling Composition (1) Manufacture of Pressure Sensors 2 to 4

A resistance-change pressure sensor operates based on change in resistance thereof according to change in a contact area between a top substrate and a bottom substrate occurring when the pressure sensor is pressed. Accordingly, it is possible that sensitivity of a pressure sensor is controllable by changing electrical characteristics of a top substrate and a bottom substrate. To do this, hybrid electronic sheets having different electric characteristics were prepared and placed on the top substrate or the bottom substrate of the pressure sensor.

In detail, pressure sensors were manufactured in the same manner as in Example 1, except that when the hybrid electron sheets for the top substrate and the bottom substrate were prepared, the phage solution including the colloid solution and the M13 phage(p8 GB#1) were prepared at molar ratios shown in Table 1. The resistance of a hybrid electronic sheet with respect to an electrode was measured as follows: a hybrid electronic sheet was transferred between two electrodes on a bottom substrate for a pressure sensor by using a stencil mask having a size of 2×2 mm and the resistance of the hybrid electronic sheet was measured by using a Fluke multi-meter. When a molar ratio of SWNT to p8 GB#1 was 8:2, the resistance of the hybrid electronic sheet was about 300Ω, and when a molar ratio of SWNT to p8 GB#1 was 2:2, the resistance of the hybrid electronic sheet was about 4300Ω. In other words, it is seen that electrical characteristics of the manufactured hybrid electronic sheet could be controlled by changing the molar ratio of SWNT to p8 GB#1.

TABLE 1

|  | Pressure sensor 1 | Pressure sensor 2 | Pressure sensor 3 | Pressure sensor 4 |
| --- | --- | --- | --- | --- |
| Top substrate | 8:2 | 2:2 | 2:2 | 8:2 |
| Bottom substrate | 8:2 | 8:2 | 2:2 | 2:2 |

To predict that it is possible to integrate and miniaturize pressure sensors 1 to 4, they were manufactured in a size of 2 mm×2 mm.

The small pressure sensor according to an exemplary embodiment can be 55 times as small as the pressure sensor manufactured according to Example 1.3. A hybrid electronic sheet according to an exemplary embodiment enables manufacture of an integrated and miniaturized pressure sensor.

(2) Analysis on Sensitivity of Pressure Sensor

To analyze sensitivity of pressure sensors 1 to 4, change in current according to pressure was measured as follows: a voltage of 0 to 20 V was applied between two electrodes, and a pressure applied was increased at an incremental rate of 1 kPa within a range of 0 to 5 kPa. Results thereof are shown in FIGS. 16 to 19.

Figure 16:
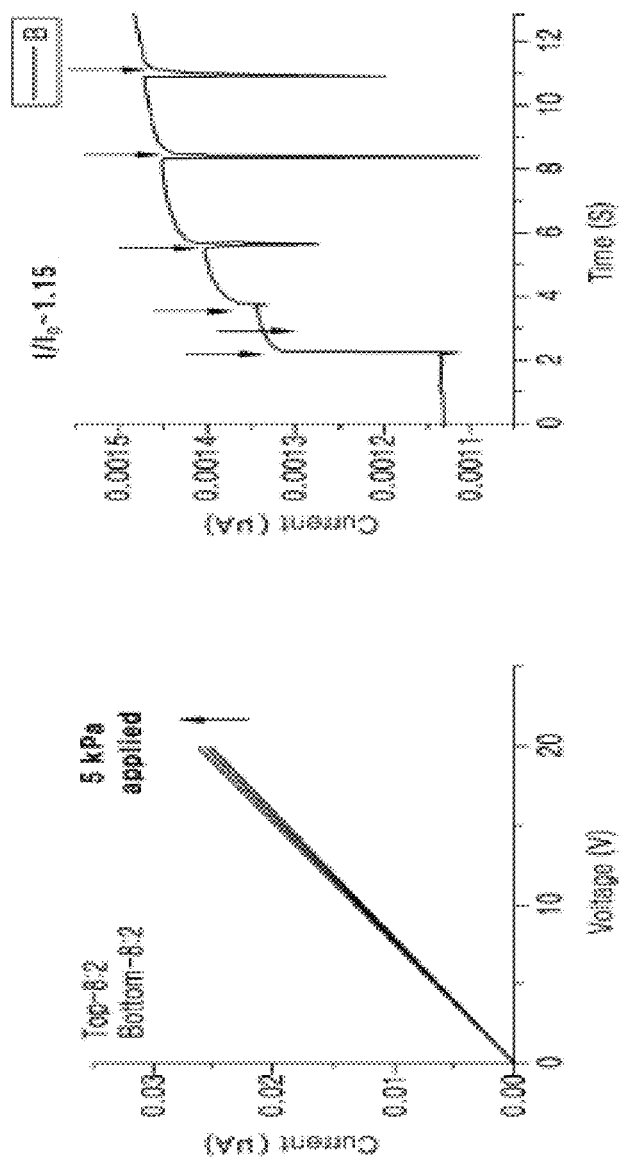
FIG. 16 illustrates a graph of current with respect to pressure when a hybrid electronic sheet made from a graphitic material and p8 GB#1 at a ratio of 8:2 transferred on a top substrate of a pressure sensor according to an exemplary embodiment and a hybrid electronic sheet made from a graphitic material and p8 GB#1 at a ratio of 8:2 transferred on a bottom substrate of the pressure sensor were pressed at an incremental pressure rate of 1 kPa, starting from 0 kPa.

FIG. 16 illustrates a graph of current with respect to pressure when a hybrid electronic sheet made from the graphitic material and p8 GB#1 at a ratio of 8:2 and transferred on a top substrate of a pressure sensor according to an exemplary embodiment and a hybrid electronic sheet made from the graphitic material and p8 GB#1 at a ratio of 8:2 and transferred on a bottom substrate of the pressure sensor were pressed at an incremental pressure rate of 1 kPa, starting from 0 kPa.

Figure 17:
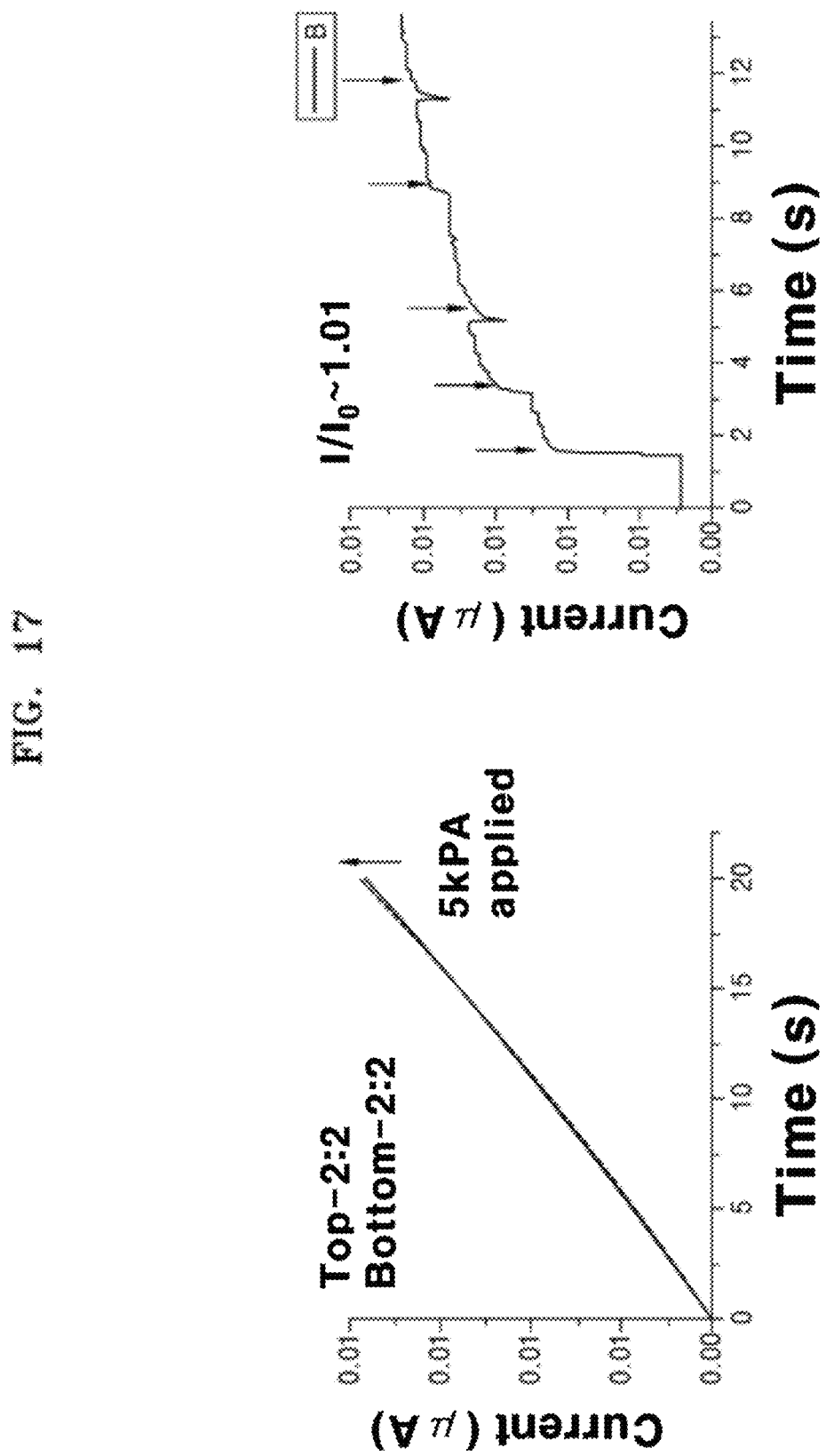
FIG. 17 illustrates a graph of current with respect to pressure when a hybrid electronic sheet made from a graphitic material and p8 GB#1 at a ratio of 2:2 transferred on a top substrate of a pressure sensor according to an exemplary embodiment and a hybrid electronic sheet made from a graphitic material and p8 GB#1 at a ratio of 8:2 transferred on a bottom substrate of the pressure sensor were pressed at an incremental pressure rate of 1 kPa, starting from 0 kPa.

FIG. 17 illustrates a graph of current with respect to pressure when a hybrid electronic sheet made from the graphitic material and p8 GB#1 at a ratio of 2:2 and transferred on a top substrate of a pressure sensor according to an exemplary embodiment and a hybrid electronic sheet made from the graphitic material and p8 GB#1 at a ratio of 8:2 and transferred on a bottom substrate of the pressure sensor were pressed at an incremental pressure rate of 1 kPa, starting from 0 kPa.

Referring to FIG. 16, in the case of the pressure sensor including the top substrate made from the graphitic material and p8 GB#1 at a ratio of 8:2 and the bottom substrate made from the graphitic material and p8 GB#1 at a ratio of 8:2, when a voltage of 1 kPa was applied to the pressure sensor, the current was increased by about 15%.

Referring to FIG. 17, in the case of the flexible pressure sensor that includes the top substrate with the hybrid electronic sheet formed using the graphitic material and p8 GB#1 at a ratio of 2:2 and transferred thereon and the bottom substrate with the hybrid electronic sheet formed using the graphitic material and p8 GB#1 at a ratio of 8:2 and transferred thereon, when a voltage of 1 kPa was applied to the pressure sensor, the current was increased by about 1%.

These results show that in the case in which the resistance of a top substrate is high, even when a contact area between the top substrate and a bottom substrate increases, due to such a high resistance, the increase in current is relatively low. That is, in the case in which the bottom substrate has high conductivity, the lower resistance the top substrate has, the higher sensitivity the pressure sensor has. Also, when a top substrate has high resistance, a pressure sensor having the top substrate has a high-pressure driving range.

Figure 18:
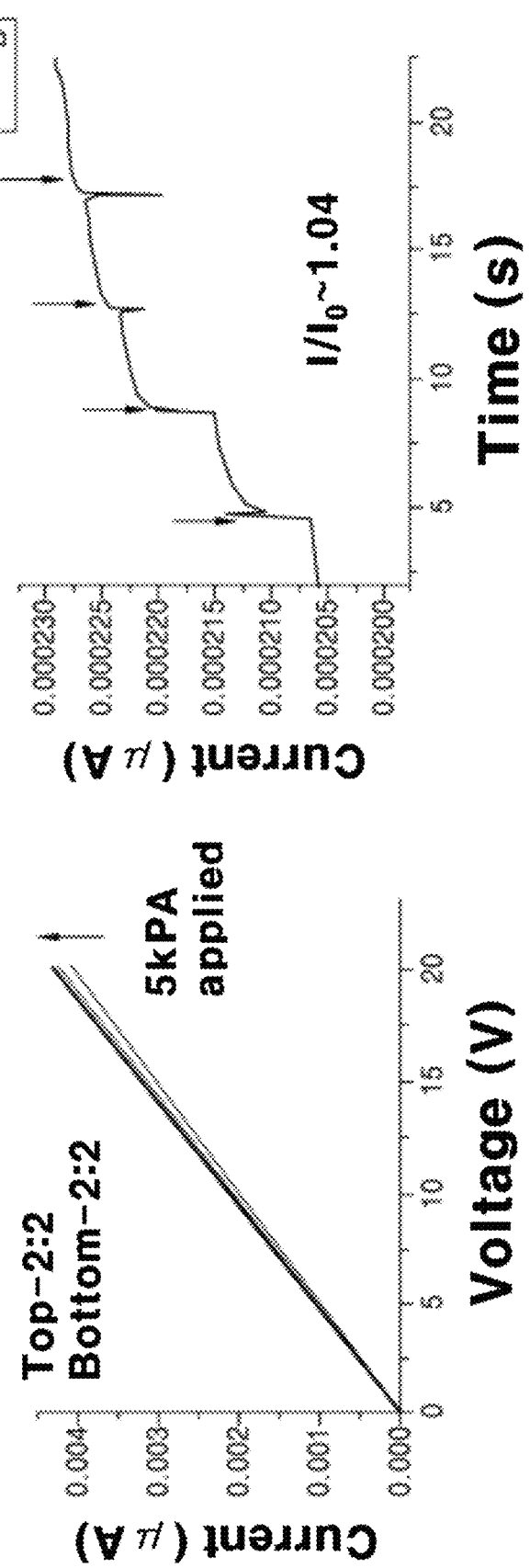
FIG. 18 illustrates a graph of current with respect to pressure when a hybrid electronic sheet made from a graphitic material and p8 GB#1 at a ratio of 2:2 transferred on a top substrate of a pressure sensor according to an exemplary embodiment and a hybrid electronic sheet made from a graphitic material and p8 GB#1 at a ratio of 2:2 transferred on a bottom substrate of the pressure sensor were pressed at an incremental pressure rate of 1 kPa, starting from 0 kPa.

FIG. 18 illustrates a graph of current with respect to pressure when a hybrid electronic sheet made from the graphitic material and p8 GB#1 at a ratio of 2:2 and transferred on a top substrate of a pressure sensor according to an exemplary embodiment and a hybrid electronic sheet made from the graphitic material and p8 GB#1 at a ratio of 2:2 transferred on a bottom substrate of the pressure sensor were pressed at an incremental rate of 1 kPa, starting form 0 kPa.

Figure 19:
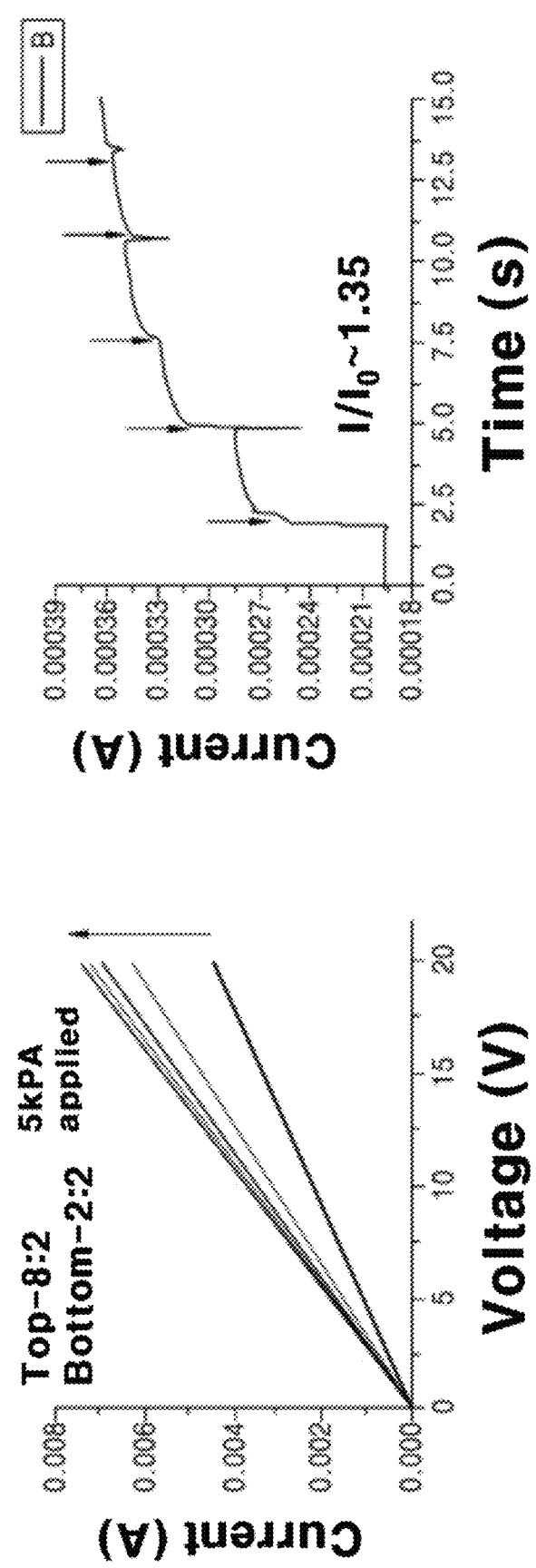
FIG. 19 illustrates a graph of current with respect to pressure when a hybrid electronic sheet made from a graphitic material and p8 GB#1 at a ratio of 8:2 transferred on a top substrate of a pressure sensor according to an exemplary embodiment and a hybrid electronic sheet made from a graphitic material and p8 GB#1 at a ratio of 2:2 transferred on a bottom substrate of the pressure sensor were pressed at an incremental pressure rate of 1 kPa, starting from 0 kPa.

FIG. 19 illustrates a graph of current with respect to pressure when a hybrid electronic sheet made from the graphitic material and p8 GB#1 at a ratio of 8:2 and transferred on a top substrate of a pressure sensor according to an exemplary embodiment and a hybrid electronic sheet made from the graphitic material and p8 GB#1 at a ratio of 2:2 and transferred on a bottom substrate of the pressure sensor were pressed at an incremental rate of 1 kPa, starting from 0 kPa.

Referring to FIG. 18, in the case of the pressure sensor that includes the top substrate with the hybrid electronic sheet formed using the graphitic material and p8 GB#1 at a ratio of 2:2 and transferred thereon and the bottom substrate with the hybrid electronic sheet formed using the graphitic material and p8 GB#1 at a ratio of 2:2 and transferred thereon, when a voltage of 1 kPa was applied to the pressure sensor, the current was increased by about 4%. This result shows that when the bottom substrate and the top substrate have high resistance, the sensitivity of the pressure sensor is lower than when the bottom substrate and the top substrate have low resistance.

Referring to FIG. 19, in the case of the pressure sensor that includes the top substrate with the hybrid electronic sheet formed using the graphitic material and p8 GB#1 at a ratio of 8:2 and transferred thereon and the bottom substrate with the hybrid electronic sheet formed using the graphitic material and p8 GB#1 at a ratio of 2:2 and transferred thereon, when a voltage of 1 kPa was applied to the pressure sensor, the current was increased by about 40%. Also, it is seen that when the resistance of the bottom substrate is high, the lower resistance the top substrate, which is to contact the bottom substrate, has, the higher sensitivity the pressure sensor has at a lower driving voltage.

From the results shown in FIGS. 16 to 19, it is seen that the sensitivity and driving range of a flexible pressure sensor are controllable by adjusting a composition of a hybrid electronic sheet. The results also show that in a pressure sensor according to an exemplary embodiment, when a top substrate is pressed, the top substrate is brought into contact with a bottom substrate, leading to a lower resistance and a higher current in the pressure sensor. This means that a driving range of the flexible pressure sensor is controllable by changing the strength or pattern structure of the top substrate.

4. Manufacture of Pressure Sensor Including Electronic Sheet Formed on Either Top Substrate or Bottom Substrate and Characteristics Analysis of the Pressure Sensor (1) Manufacture of Pressure Sensor 5

To manufacture a pressure sensor including a hybrid electronic sheet transferred only on a top substrate, a pressure sensor was manufactured in the same manner as used to manufacture the pressure sensor 1, except that a conductive polymer was coated on the bottom substrate.

In detail, to manufacture a bottom substrate coated with a conductive polymer PEDOT:PSS (poly(3,4-ethylenedioxythiophene) polystyrene sulfonate), a PDMS polymer substrate was used as the bottom substrate. Sylgard® 184 silicon elastomer and a Sylgard® 184 silicon elastomer curing agent were mixed at a ratio of 10:1, and then, a thickness of the result was adjusted by petri-dish spin coating, and curing was performed thereon in an oven at a temperature of 70° C. for about 6 hours. The cured PDMS film was cut to a desired size by using a knife for surgery. On the separated flexible polymer PDMS film, a Stencil mask was mounted, and then, a metal electrode (Pt) was placed thereon by sputtering. A PEDOT:PSS solution was dropped portionwise between deposited two electrodes, and then, spin coating was performed thereon at a 3000 rpm to complete the manufacture of the bottom substrate having conductivity. For stability of the bottom substrate, the bottom substrate was heat treated in an oven at a temperature of 80° C. for about 10 minutes.

A top substrate having a pyramid structure was manufactured by silicon wafer etching. In detail, a silicon substrate was patterned by using an exposure process to have a tetragonal pattern, and buffered oxide etching (BOE) was performed thereon for 10 minutes to remove silicon oxide, and then, 30% KOH etching was performed thereon to manufacture a pyramid structure. A height of the pyramid structure was about 100 um. Sylgard® 184 silicon elastomer and Sylgard® 184 silicon elastomer curing agent were mixed at a ratio of 10:1, and then, a petridish spin coating method was used to adjust the thickness of the resultant. Then, in an oven at a temperature of 70° C., curing was performed thereon for about 6 hours. The hardened PDMS film was cut to a target size by using an operating knife. A hybrid electronic sheet made from a graphitic material and p8 GB#1 at a ratio of 5:2 was transferred onto the top substrate having the pyramid structure by using a stencil mask, and then, dried for about one hour in air. The hybrid electronic sheet transferred on the polymer film of the top substrate was washed with distilled water after removing the stencil mask, and then dried by using nitrogen gas. Then, the bottom substrate with PEDOT:PSS coated thereon was folded with the top substrate with the hybrid electronic sheet coated thereon, the resultant structure was packaged by using a polymer material having sticky properties, thereby completing manufacture of a flexible pressure device. For device packaging, in the same manner as used to manufacture the bottom substrate, a PDMS solution was doped on outside a top/bottom substrate PDMS substrate, and then cured at a temperature of 80° C. for about 30 minutes. Also, instead of the PDMS solution, an epoxy curing agent/a polyacrylate polymer adhesive were used to bind two PDMS polymer substrates together.

(2) Analysis of Sensitivity of Pressure Sensor

A current change with respect to pressure was measured in such a way that 0-10 V of voltage was applied to two electrodes of the pressure sensor 5, while 0 to 5 kPa of pressure was applied thereto at an incremental rate of 1 kPa. Results thereof are shown in FIG. 20.

Figure 20:
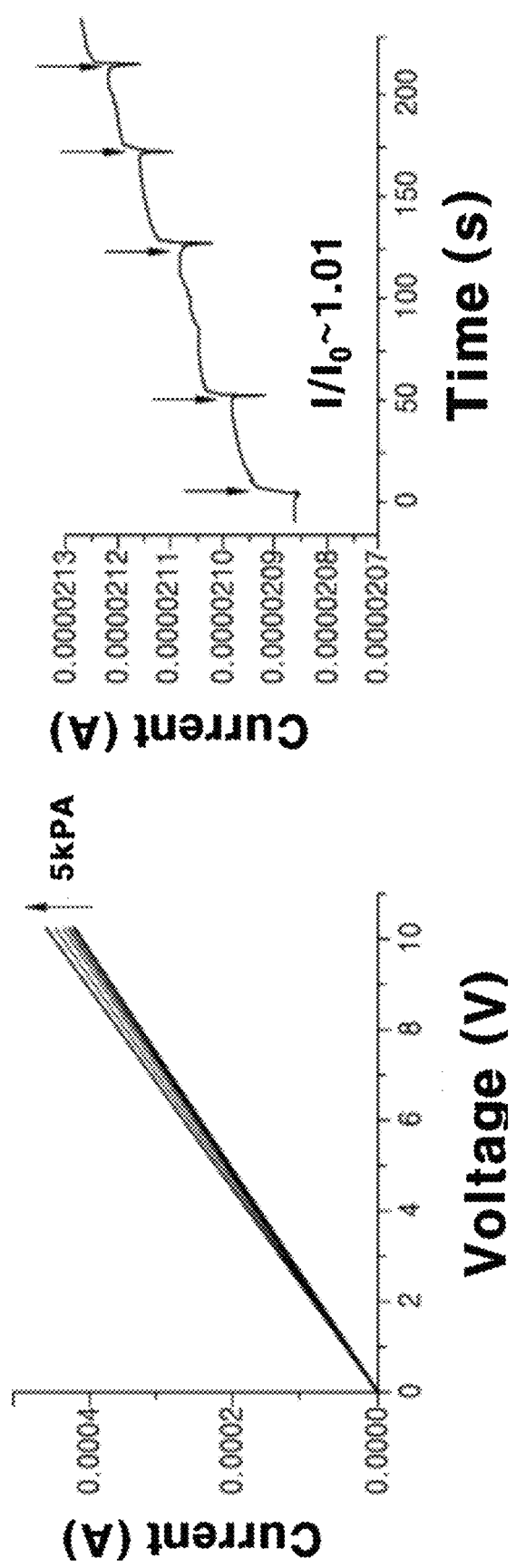
FIG. 20 illustrates a graph of current when a hybrid electronic sheet made from a graphitic material and p8 GB#1 at a ratio of 5:2 transferred on a top substrate of a pressure sensor according to an exemplary embodiment and poly(3,4-ethylenedioxythiophene) polystyrene sulfonate (PEDOT:PSS) transferred on a bottom substrate were pressed at an incremental pressure rate of 1 kPa, starting from 0 kPa.

FIG. 20 illustrates a graph of current when 0 to 1 kPa of pressure was incrementally applied to a pressure sensor 5 according to an embodiment including a top substrate with a hybrid electronic sheet made from graphitic material and p8 GB#1 at a ratio of 5:2 and transferred thereon and a bottom substrate having PEDOT:PSS transferred thereon.

Referring to FIG. 20, in the case of a flexible pressure device in which a hybrid electronic sheet made from a graphitic material and p8 GB#1 at a ratio of 5:2 is transferred on a top substrate and PEDOT:PSS is transferred on a bottom substrate, it is seen that when about 1 kPa of pressure was applied, the current was increased by about 1% current. This result shows that even when a hybrid electronic sheet is transferred on at least one of the top substrate and the bottom substrate, the flexible pressure device still works.

Pressure sensors according to embodiments have excellent controllable electric properties, and mechanical flexibility and stability, and can be used to measure, for example, pressure in an easy and highly reproducible manner in which resistance of a component in the pressure sensor is changed when pressure is applied thereto.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the inventive concept as defined by the following claims.

What is claimed is:

1. A pressure sensor comprising
a bottom substrate;
a top substrate located on the bottom substrate and spaced apart from at least a portion of the bottom substrate; an electrode formed on at least a portion of the bottom substrate or at least a portion of the top substrate; and a first electronic sheet directly formed on at least a portion of the bottom substrate and a second electronic sheet directly formed on at least a portion of a surface of the top substrate facing the bottom substrate, wherein the first electronic sheet and the second electronic sheet, respectively, comprises a graphitic material and a phage binding to the graphitic material, and the binding is made between a peptide displayed on a coat protein or a fragment thereof of the phage and the graphitic material; and
wherein at least a portion of the first electronic sheet contacts at least a portion of the second electronic sheet.

2. The pressure sensor of claim 1, wherein the bottom substrate or the top substrate has an uneven repeating surface pattern wherein a portion of the repeating surface pattern has a triangular, tetragonal, or circular cross-section.

3. The pressure sensor of claim 1, wherein the bottom substrate or the top substrate has an uneven surface pattern having a convex portion and a concave portion.

4. The pressure sensor of claim 3, wherein both the bottom substrate and the top substrate have the uneven surface pattern having the convex portion and the concave portion, wherein at least a portion of the first or second electronic sheet on the convex portion of the bottom or top substrate contacts at least a portion of the other of the first or second electronic sheet on the convex portion or the concave portion of the other of the bottom or top substrate.

5. The pressure sensor of claim 1, wherein the bottom substrate or the top substrate comprises a flexible substrate.

6. The pressure sensor of claim 1, further comprising a cover covering the bottom substrate or the top substrate.

7. The pressure sensor of claim 1, wherein a contact area, a contact distance or a conductive network density of the first electronic sheet and the second electronic sheet is dependent on pressure applied to the bottom substrate and the top substrate, respectively.

8. The pressure sensor of claim 1, wherein a number ratio of the graphitic material to the phage in the first electronic sheet or second electronic sheet is in a range of 1:10 to 10:1.

9. The pressure sensor of claim 1, wherein a resistance value of the first electronic sheet is equal to or greater than a resistance value of the second electronic sheet.

10. The pressure sensor of claim 1, wherein a resistance value of the first electronic sheet is less than a resistance value of the second electronic sheet.

11. The pressure sensor of claim 1, wherein an interior structure of the first and second electronic sheets comprises a percolated network structure.

12. The pressure sensor of claim 1, wherein the graphitic material comprises at least one selected from a graphene sheet, a highly oriented pyrolytic graphite (HOPG) sheet, a graphene oxide, a reduced graphene oxide, a single-walled carbon nanotube, a double-walled carbon nanotube, a multi-walled carbon nanotube, and fullerene.

13. The pressure sensor of claim 1, wherein the graphitic material comprises a combination of a graphene sheet and a single-walled carbon nanotube.

14. The pressure sensor of claim 1, wherein the peptide has a least one sequence selected from amino acid sequences set forth in SEQ ID NO. 1 to SEQ ID NO. 8.

15. The pressure sensor of claim 1, wherein the phage is genetically engineered to have a binding property to the graphitic material.

16. The pressure sensor of claim 1, wherein the phage comprises M13 phage, F1 phage, Fd phage, If1 phage, Ike phage, Zj/Z phage, Ff phage, Xf phage, Pf1 phage, or Pf3 phage.

17. The pressure sensor of claim 1, wherein the pressure sensor is to measure blood pressure or a heart rate.

18. A wearable device comprising the pressure sensor of claim 1.

* * * * *

SEQUENCE LISTING

```
<160> NUMBER OF SEQ ID NOS: 14

<210> SEQ ID NO 1
<211> LENGTH: 8
<212> TYPE: PRT
<213> ORGANISM: Artificial Sequence
<220> FEATURE:
<223> OTHER INFORMATION: peptide selectively binding to graphitic
      materials
<220> FEATURE:
<221> NAME/KEY: VARIANT
<222> LOCATION: (1)..(1)
<223> OTHER INFORMATION: X is D, E, N, or Q
<220> FEATURE:
<221> NAME/KEY: VARIANT
<222> LOCATION: (3)..(3)
<223> OTHER INFORMATION: X is W, Y, F or H
<220> FEATURE:
<221> NAME/KEY: VARIANT
<222> LOCATION: (6)..(6)
<223> OTHER INFORMATION: X is D, E, N or Q
<220> FEATURE:
<221> NAME/KEY: VARIANT
<222> LOCATION: (7)..(7)
<223> OTHER INFORMATION: X is I, L, or V

<400> SEQUENCE: 1

Xaa Ser Xaa Ala Ala Xaa Xaa Pro
1               5

<210> SEQ ID NO 2
<211> LENGTH: 8
<212> TYPE: PRT
<213> ORGANISM: Artificial Sequence
<220> FEATURE:
<223> OTHER INFORMATION: peptide selectively binding to graphitic
      materials
<220> FEATURE:
<221> NAME/KEY: VARIANT
<222> LOCATION: (1)..(1)
<223> OTHER INFORMATION: X is D, E, N, or Q
<220> FEATURE:
<221> NAME/KEY: VARIANT
<222> LOCATION: (2)..(2)
<223> OTHER INFORMATION: X is D, E, N, or Q
<220> FEATURE:
<221> NAME/KEY: VARIANT
<222> LOCATION: (4)..(4)
<223> OTHER INFORMATION: X is I, L, or V
<220> FEATURE:
<221> NAME/KEY: VARIANT
<222> LOCATION: (5)..(5)
<223> OTHER INFORMATION: X is D, E, N, or Q
```

```
<220> FEATURE:
<221> NAME/KEY: VARIANT
<222> LOCATION: (7)..(7)
<223> OTHER INFORMATION: X is I, L, or V

<400> SEQUENCE: 2

Xaa Xaa Pro Xaa Xaa Ala Xaa Pro
1               5

<210> SEQ ID NO 3
<211> LENGTH: 7
<212> TYPE: PRT
<213> ORGANISM: Artificial Sequence
<220> FEATURE:
<223> OTHER INFORMATION: peptide selectively binding to graphitic
      materials
<220> FEATURE:
<221> NAME/KEY: VARIANT
<222> LOCATION: (2)..(2)
<223> OTHER INFORMATION: X is W, Y, F, or H
<220> FEATURE:
<221> NAME/KEY: VARIANT
<222> LOCATION: (5)..(5)
<223> OTHER INFORMATION: X is D, E, N, or Q
<220> FEATURE:
<221> NAME/KEY: VARIANT
<222> LOCATION: (6)..(6)
<223> OTHER INFORMATION: X is I, L, or V

<400> SEQUENCE: 3

Ser Xaa Ala Ala Xaa Xaa Pro
1               5

<210> SEQ ID NO 4
<211> LENGTH: 7
<212> TYPE: PRT
<213> ORGANISM: Artificial Sequence
<220> FEATURE:
<223> OTHER INFORMATION: peptide selectively binding to graphitic
      materials
<220> FEATURE:
<221> NAME/KEY: VARIANT
<222> LOCATION: (1)..(1)
<223> OTHER INFORMATION: X is D, E, N, or Q
<220> FEATURE:
<221> NAME/KEY: VARIANT
<222> LOCATION: (3)..(3)
<223> OTHER INFORMATION: X is I, L, or V
<220> FEATURE:
<221> NAME/KEY: VARIANT
<222> LOCATION: (4)..(4)
<223> OTHER INFORMATION: X is D, E, N, or Q
<220> FEATURE:
<221> NAME/KEY: VARIANT
<222> LOCATION: (6)..(6)
<223> OTHER INFORMATION: X is I, L, or V

<400> SEQUENCE: 4

Xaa Pro Xaa Xaa Ala Xaa Pro
1               5

<210> SEQ ID NO 5
<211> LENGTH: 8
<212> TYPE: PRT
<213> ORGANISM: Artificial Sequence
<220> FEATURE:
<223> OTHER INFORMATION: peptide selectively binding to graphitic
      materials

<400> SEQUENCE: 5

Asp Ser Trp Ala Ala Asp Ile Pro
1               5
```

```
<210> SEQ ID NO 6
<211> LENGTH: 8
<212> TYPE: PRT
<213> ORGANISM: Artificial Sequence
<220> FEATURE:
<223> OTHER INFORMATION: peptide selectively binding to graphitic
      materials

<400> SEQUENCE: 6

Asp Asn Pro Ile Gln Ala Val Pro
1               5

<210> SEQ ID NO 7
<211> LENGTH: 7
<212> TYPE: PRT
<213> ORGANISM: Artificial Sequence
<220> FEATURE:
<223> OTHER INFORMATION: peptide selectively binding to graphitic
      materials

<400> SEQUENCE: 7

Ser Trp Ala Ala Asp Ile Pro
1               5

<210> SEQ ID NO 8
<211> LENGTH: 7
<212> TYPE: PRT
<213> ORGANISM: Artificial Sequence
<220> FEATURE:
<223> OTHER INFORMATION: peptide selectively binding to graphitic
      materials

<400> SEQUENCE: 8

Asn Pro Ile Gln Ala Val Pro
1               5

<210> SEQ ID NO 9
<211> LENGTH: 7222
<212> TYPE: DNA
<213> ORGANISM: Artificial Sequence
<220> FEATURE:
<223> OTHER INFORMATION: cloning vector M13KE

<400> SEQUENCE: 9
aatgctacta ctattagtag aattgatgcc acctttttcag ctcgcgcccc aaatgaaaat     60
atagctaaac aggttattga ccatttgcga aatgtatcta atggtcaaac taaatctact    120
cgttcgcaga attgggaatc aactgttata tggaatgaaa cttccagaca ccgtacttta    180
gttgcatatt taaaacatgt tgagctacag cattatattc agcaattaag ctctaagcca    240
tccgcaaaaa tgacctctta tcaaaaggag caattaaagg tactctctaa tcctgacctg    300
ttggagtttg cttccggtct ggttcgcttt gaagctcgaa ttaaaacgcg atatttgaag    360
tctttcgggc ttcctcttaa tctttttgat gcaatccgct ttgcttctga ctataatagt    420
cagggtaaag acctgatttt tgatttatgg tcattctcgt tttctgaact gtttaaagca    480
tttgaggggg attcaatgaa tatttatgac gattccgcag tattggacgc tatccagtct    540
aaacatttta ctattacccc ctctggcaaa acttcttttg caaaagcctc tcgctatttt    600
ggtttttatc gtcgtctggt aaacgagggt tatgatagtg ttgctcttac tatgcctcgt    660
aattcctttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
```

```
caatgattaa agttgaaatt aaaccatctc aagcccaatt tactactcgt tctggtgttt      900
ctcgtcaggg caagccttat tcactgaatg agcagctttg ttacgttgat ttgggtaatg      960
aatatccggt tcttgtcaag attactcttg atgaaggtca gccagcctat gcgcctggtc     1020
tgtacaccgt tcatctgtcc tctttcaaag ttggtcagtt cggttccctt atgattgacc     1080
gtctgcgcct cgttccggct aagtaacatg gagcaggtcg cggatttcga cacaatttat     1140
caggcgatga tacaaatctc cgttgtactt tgtttcgcgc ttggtataat cgctggggt      1200 caaagatgag tgttttagtg tattcttttg cctctttcgt tttaggttgg tgccttcgta     1260
gtggcattac gtattttacc cgtttaatgg aaacttcctc atgaaaaagt ctttagtcct     1320
caaagcctct gtagccgttg ctaccctcgt tccgatgctg tctttcgctg ctgagggtga     1380
cgatcccgca aaagcggcct taactccct gcaagcctca gcgaccgaat atatcggtta      1440
tgcgtgggcg atggttgttg tcattgtcgg cgcaactatc ggtatcaagc tgtttaagaa     1500
attcacctcg aaagcaagct gataaaccga tacaattaaa ggctccttt ggagccttt       1560 ttttggagat tttcaacgtg aaaaaattat tattcgcaat tcctttagtg gtacctttct     1620
attctcactc ggccgaaact gttgaaagtt gtttagcaaa atcccataca gaaaattcat     1680
ttactaacgt ctggaaagac gacaaaactt tagatcgtta cgctaactat gagggctgtc     1740
tgtggaatgc tacaggcgtt gtagtttgta ctggtgacga aactcagtgt tacggtacat     1800
gggttcctat gggcttgct atccctgaaa atgagggtgg tggctctgag ggtggcggtt      1860
ctgagggtgg cggttctgag ggtggcggta ctaaacctcc tgagtacggt gatacaccta     1920
ttccgggcta tacttatatc aaccctctcg acggcactta ccgcctggt actgagcaaa      1980 accccgctaa tcctaatcct tctcttgagg agtctcagcc tcttaatact ttcatgtttc     2040
agaataatag gttccgaaat aggcaggggg cattaactgt ttatacgggc actgttactc     2100
aaggcactga ccccgttaaa acttattacc agtacactcc tgtatcatca aaagccatgt     2160
atgacgctta ctggaacggt aaattcagag actgcgcttt ccattctggc tttaatgagg     2220
atttatttgt ttgtgaatat caaggccaat cgtctgacct gcctcaacct cctgtcaatg     2280
ctggcggcgg ctctggtggt ggttctggtg gcggctctga gggtggtggc tctgagggtg     2340
gcggttctga gggtggcggc tctgagggag gcggttccgg tggtggctct ggttccggtg     2400
attttgatta tgaaaagatg gcaaacgcta ataaggggc tatgaccgaa aatgccgatg      2460
aaaacgcgct acagtctgac gctaaaggca aacttgattc tgtcgctact gattacggtg     2520
ctgctatcga tggtttcatt ggtgacgttt ccggccttgc taatggtaat ggtgctactg     2580
gtgattttgc tggctctaat tcccaaatgg ctcaagtcgg tgacggtgat aattcacctt     2640
taatgaataa tttccgtcaa tatttacctt ccctccctca atcggttgaa tgtcgccctt     2700
ttgtctttgg cgctggtaaa ccatatgaat tttctattga ttgtgacaaa ataaacttat     2760
tccgtggtgt ctttgcgttt cttttatatg ttgccacctt tatgtatgta ttttctacgt     2820
ttgctaacat actgcgtaat aaggagtctt aatcatgcca gttcttttgg gtattccgtt     2880
attattgcgt ttcctcggtt tccttctggt aactttgttc ggctatctgc ttacttttct     2940 taaaagggc ttcggtaaga tagctattgc tatttcattg tttcttgctc ttattattgg     3000
gcttaactca attcttgtgg gttatctctc tgatattagc gctcaattac cctctgactt     3060
tgttcagggt gttcagttaa ttctcccgtc taatgcgctt ccctgttttt atgttattct     3120
ctctgtaaag gctgctattt tcattttga cgttaaacaa aaaatcgttt cttatttgga     3180
ttgggataaa taatatggct gtttattttg taactggcaa attaggctct ggaaagacgc     3240
```

-continued

```
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
cccgttcttg gaatgataag gaaagacagc cgattattga ttggtttcta catgctcgta    3540
aattaggatg ggatattatt tttcttgttc aggacttatc tattgttgat aaacaggcgc    3600
gttctgcatt agctgaacat gttgtttatt gtcgtcgtct ggacagaatt actttacctt    3660
ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc tttttctagt aattatgatt    3840
ccggtgttta ttcttatttta acgccttatt tatcacacgg tcggtatttc aaaccattaa    3900
atttaggtca gaagatgaaa ttaactaaaa tatatttgaa aaagttttct cgcgttcttt    3960
gtcttgcgat tggatttgca tcagcattta catatagtta tataacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta atgtaatta attttgtttt cttgatgttt    4260
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg caaataattt tgatatggta ggttctaacc cttccattat tcagaagtat    4500
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg gctctaatct attagttgtt    4740
agtgctccta aagatatttt agataacctt cctcaattcc tttcaactgt tgatttgcca    4800
actgaccaga tattgattga gggttttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta ttttaatgg cgatgtttta    4980 gggctatcag ttcgcgcatt aaagactaat agccattcaa aaatattgtc tgtgccacgt    5040
attcttacgc tttcaggtca gaagggttct atctctgttg gccagaatgt cctttttatt    5100
actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
ggtggcctca ctgattataa aaacacttct caggattctg cgtaccgttc ctgtctaaaa    5400
atccctttaa tcggcctcct gtttagctcc cgctctgatt ctaacgagga aagcacgtta    5460
tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt cccgtcaag ctctaaatcg    5640
```

```
ggggctccct ttagggttcc gatttagtgc tttacggcac ctcgacccca aaaaacttga    5700
tttgggtgat ggttcacgta gtgggccatc gccctgatag acggttttc gcccttttgac   5760 gttggagtcc acgttcttta atagtggact cttgttccaa actggaacaa cactcaaccc   5820
tatctcgggc tattcttttg atttataagg gattttgccg atttcggaac caccatcaaa   5880
caggattttc gcctgctggg gcaaaccagc gtggaccgct tgctgcaact ctctcagggc   5940
caggcggtga agggcaatca gctgttgccc gtctcactgg tgaaaagaaa aaccaccctg   6000
gcgcccaata cgcaaaccgc ctctccccgc gcgttggccg attcattaat gcagctggca   6060
cgacaggttt cccgactgga aagcgggcag tgagcgcaac gcaattaatg tgagttagct   6120
cactcattag gcaccccagg ctttacactt tatgcttccg gctcgtatgt tgtgtggaat   6180
tgtgagcgga taacaatttc acacaggaaa cagctatgac catgattacg ccaagcttgc   6240
atgcctgcag gtcctcgaat tcactggccg tcgttttaca acgtcgtgac tgggaaaacc   6300
ctggcgttac ccaacttaat cgccttgcag cacatccccc tttcgccagc tggcgtaata   6360
gcgaagaggc ccgcaccgat cgcccttccc aacagttgcg cagcctgaat ggcgaatggc   6420
gctttgcctg gtttccggca ccagaagcgg tgccggaaag ctggctggag tgcgatcttc   6480
ctgaggccga tactgtcgtc gtcccctcaa actggcagat gcacggttac gatgcgccca   6540
tctacaccaa cgtgacctat cccattacgg tcaatccgcc gtttgttccc acggagaatc   6600
cgacgggttg ttactcgctc acatttaatg ttgatgaaag ctggctacag gaaggccaga   6660
cgcgaattat ttttgatggc gttcctattg gttaaaaaat gagctgattt aacaaaaatt   6720
taatgcgaat tttaacaaaa tattaacgtt tacaatttaa atatttgctt atacaatctt   6780 cctgttttg gggcttttct gattatcaac cggggtacat atgattgaca tgctagtttt   6840
acgattaccg ttcatcgatt ctcttgtttg ctccagactc tcaggcaatg acctgatagc   6900
ctttgtagat ctctcaaaaa tagctaccct ctccggcatt aatttatcag ctagaacggt   6960
tgaatatcat attgatggtg atttgactgt ctccggcctt tctcacccct ttgaatcttt   7020
acctacacat tactcaggca ttgcatttaa aatatatgag ggttctaaaa attttttatcc   7080 ttgcgttgaa ataaaggctt ctcccgcaaa agtattacag ggtcataatg tttttggtac   7140
aaccgattta gctttatgct ctgaggcttt attgcttaat tttgctaatt ctttgccttg   7200
cctgtatgat ttattggatg tt                                            7222

<210> SEQ ID NO 10
<211> LENGTH: 41
<212> TYPE: DNA
<213> ORGANISM: Artificial Sequence
<220> FEATURE:
<223> OTHER INFORMATION: BamH I_SM_upper which is a primer used for
      site-directed mutation

<400> SEQUENCE: 10
aaggccgctt tgcgggatc ctcaccctca gcagcgaaag a                         41

<210> SEQ ID NO 11
<211> LENGTH: 41
<212> TYPE: DNA
<213> ORGANISM: Artificial Sequence
<220> FEATURE:
<223> OTHER INFORMATION: BamH I_SM_lower which is a primer used for
      site-directed mutation

<400> SEQUENCE: 11
tctttcgctg ctgagggtga ggatcccgca aaagcggcct t                        41
```

```
<210> SEQ ID NO 12
<211> LENGTH: 90
<212> TYPE: DNA
<213> ORGANISM: Artificial Sequence
<220> FEATURE:
<223> OTHER INFORMATION: BamM13HK_P8_primer which is an extension primer
      used for preparation

<400> SEQUENCE: 12
ttaatggaaa cttcctcatg aaaaagtctt tagtcctcaa agcctctgta gccgttgcta        60
ccctcgttcc gatgctgtct ttcgctgctg                                        90

<210> SEQ ID NO 13
<211> LENGTH: 95
<212> TYPE: DNA
<213> ORGANISM: Artificial Sequence
<220> FEATURE:
<223> OTHER INFORMATION: M13HK_P8 which is a library oligonucleotide
      used for preparation
<220> FEATURE:
<221> NAME/KEY: misc_feature
<222> LOCATION: (1)..(95)
<223> OTHER INFORMATION: n is a, g, c or t
<220> FEATURE:
<221> NAME/KEY: misc_feature
<222> LOCATION: (1)..(95)
<223> OTHER INFORMATION: m is a or c

<400> SEQUENCE: 13
aaggccgctt ttgcgggatc cnnmnmnmnm nmnnmnmnmn nmncagcagc gaaagacagc        60
atcggaacga gggtagcaac ggctacagag gcttt                                  95

<210> SEQ ID NO 14
<211> LENGTH: 50
<212> TYPE: PRT
<213> ORGANISM: Artificial Sequence
<220> FEATURE:
<223> OTHER INFORMATION: P8 protein of M13 phage

<400> SEQUENCE: 14

Ala Glu Gly Asp Asp Pro Ala Lys Ala Ala Phe Asn Ser Leu Gln Ala
1               5                   10                  15

Ser Ala Thr Glu Tyr Ile Gly Tyr Ala Trp Ala Met Val Val Val Ile
            20                  25                  30

Val Gly Ala Thr Ile Gly Ile Lys Leu Phe Lys Lys Phe Thr Ser Lys
        35                  40                  45

Ala Ser
    50
```